United States Patent
Aparin et al.

(10) Patent No.: US 12,163,172 B2
(45) Date of Patent: Dec. 10, 2024

(54) REAGENTS AND METHODS USED IN DEPROTECTION OF 3'-O-AMINO POLYNUCLEOTIDES

(71) Applicant: DNA Script, Le Kremlin-Bicêtre (FR)

(72) Inventors: Ilya Aparin, Le Kremlin-Bicêtre (FR); Mikhael Soskine, Le Kremlin-Bicêtre (FR); Weidong Wu, Le Kremlin-Bicêtre (FR); Adeline Veillet, Le Kremlin-Bicêtre (FR)

(73) Assignee: DNA SCRIPT, Le Kremlin-Bicêtre (FR)

( * ) Notice: Subject to any disclaimer, the term of this patent is extended or adjusted under 35 U.S.C. 154(b) by 0 days.

(21) Appl. No.: 18/654,906

(22) Filed: May 3, 2024

(65) Prior Publication Data
US 2024/0368656 A1 Nov. 7, 2024

(30) Foreign Application Priority Data

May 3, 2023 (EP) .................................... 23315154
Jul. 20, 2023 (EP) .................................... 23186636

(51) Int. Cl.
| | | |
|---|---|---|
| *C12P 19/34* | (2006.01) | |
| *C07F 9/38* | (2006.01) | |
| *C12N 9/12* | (2006.01) | |
| *C12N 15/10* | (2006.01) | |
| *C12Q 1/6806* | (2018.01) | |
| *C12Q 1/6869* | (2018.01) | |

(52) U.S. Cl.
CPC ............ *C12P 19/34* (2013.01); *C07F 9/3847* (2013.01); *C12N 9/1264* (2013.01); *C12N 15/1096* (2013.01); *C12Q 1/6806* (2013.01); *C12Q 1/6869* (2013.01)

(58) Field of Classification Search
CPC ... C12N 9/1264; C12N 15/1096; C12P 19/34; C12Q 1/6806; C12Q 1/6869; C07F 9/3847
USPC ............. 435/6.1, 91.1, 91.31; 536/23.1, 24.5
See application file for complete search history.

(56) References Cited

PUBLICATIONS

Fox et al (J. Cancer Res. Clin. Oncol., vol. 122, pp. 78-94 (1996)) (Year: 1996).*
Nolan et al, FEMS Microbiology Letters, vol. 95, pp. 71-76 (1992)) (Year: 1992).*

* cited by examiner

*Primary Examiner* — Jane J Zara
(74) *Attorney, Agent, or Firm* — WC&F IP

(57) ABSTRACT

This disclosure relates to an enzymatic method of synthesizing a polynucleotide, comprising a deprotecting step which uses as a deprotecting agent a specific phosphonate compound. It also pertains to a method for deprotecting 3'-O-amino elongated fragments of a polynucleotide in an enzymatic method of synthesizing a polynucleotide, comprising contacting the elongated fragments with this phosphonate compound. This disclosure further relates to a kit for synthesizing a polynucleotide comprising one or more vials of synthesis reagents, at least one of which contains an effective amount of a phosphonate compound and to a specific method for preparing said phosphonate compound.

13 Claims, 16 Drawing Sheets
Specification includes a Sequence Listing.

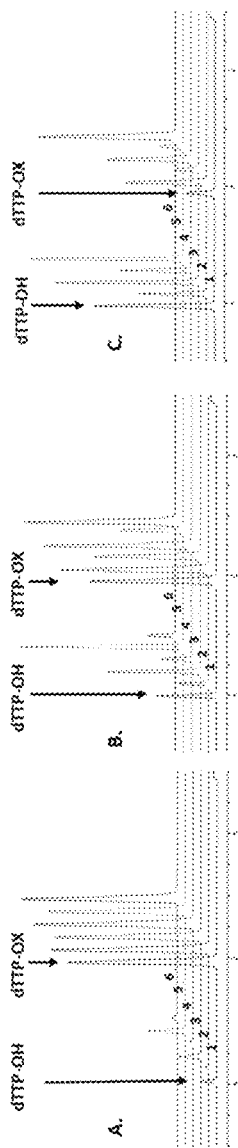
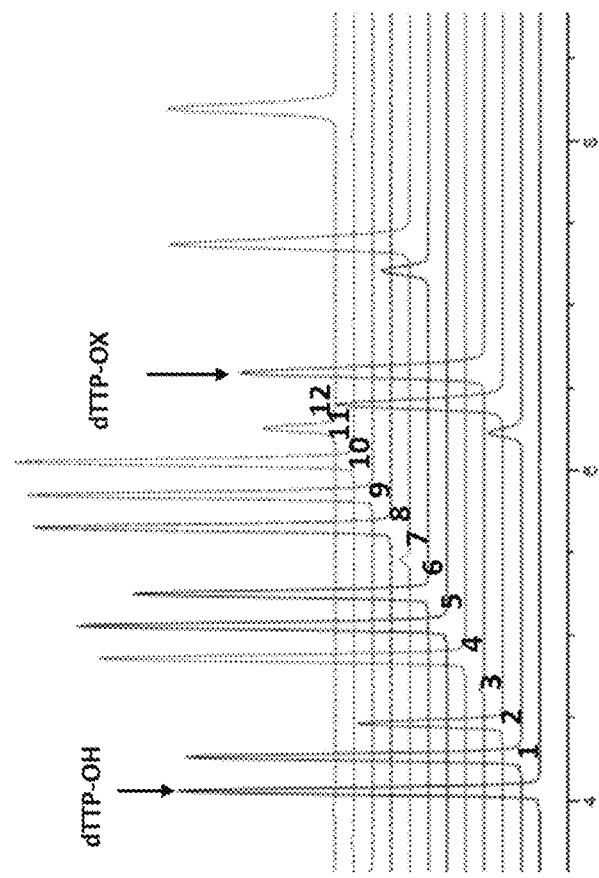
FIG. 4A
FIG. 4B

REAGENTS AND METHODS USED IN DEPROTECTION OF 3'-O-AMINO POLYNUCLEOTIDES

RELATED APPLICATIONS

This application claims priority to EP 23315154.7 filed on May 3, 2023 and EP 23186636.9 filed on Jul. 20, 2023, which are each incorporated into this application in their entirety.

FIELD OF THE DISCLOSURE

This disclosure relates to an enzymatic method of synthesizing a polynucleotide, comprising a deprotecting step which uses as a deprotecting agent a specific phosphonate compound. It also pertains to a method for deprotecting 3'-O-amino elongated fragments of a polynucleotide in an enzymatic method of synthesizing a polynucleotide, comprising contacting the elongated fragments with this phosphonate compound. This disclosure further relates to a kit for synthesizing a polynucleotide which contains an effective amount of a phosphonate compound and to a specific method for preparing said phosphonate compound.

BACKGROUND

Interest in enzymatic approaches to polynucleotide synthesis has increased not only because of increased demand for synthetic polynucleotides in many areas, such as synthetic biology (e.g. synthesis of insulin for the treatment of diabetes), CRISPR-Cas9 applications, and next generation sequencing (such as "sequencing by synthesis" or SBS, and "sequencing by binding" or SBB), but also because of the limitations of chemical approaches to polynucleotide synthesis, such as upper limits on product length, the use of moisture-sensitive monomers and the use of environmentally unfriendly solvents (Jensen et al, *Biochemistry*, 57:1821-1832, 2018).

Currently, most enzymatic approaches for both DNA and RNA synthesis employ polymerases that are used to implement repeated cycles of elongating an initiator polynucleotide by coupling with a 3'-O protected nucleotide, such as 3'-O-amino nucleotide, then deprotecting the protected growing strand thus obtained, until an elongated polynucleotide of the desired sequence is obtained. For example, TdT variants have been engineered (WO96/07669) that efficiently incorporate into growing polynucleotide strands reversibly protected 3'-O-amino nucleoside triphosphate monomers developed by Steven Benner (Champion et al, U.S. Pat. No. 10,752,887 and WO2020/099451; Benner et al, U.S. Pat. Nos. 7,544,794, 8,034,923, 8,212,020 and 10,472,383, and Hutter et al, *Nucleosides Nucleotides Nucleic Acids*, 29 (11): 879-895, 2010). The utility of the —$ONH_2$ chemical moiety as a protecting group rests in its ability to reversibly mask the 3'-OH group on 2-deoxyribose or ribose nucleoside. Additionally, the small size of the —$ONH_2$ chemical moiety makes it a better substrate for enzymes such as polymerases.

It has been suggested that the deprotecting agent used for converting the 3'-$ONH_2$ group of the protected oligonucleotide formed in each cycle into a 3-OH group may be selected among: oxidants such as hypochlorite, nitric oxide, sodium nitrite buffered to a pH of about 5.5 (Daniel Hutter et al., *Nucleosides, Nucleotides and Nucleic Acids*, 29:879-895, 2010), nitrous acid at pH 4-5, nitrite esters at pH 7-8, iodates, periodates, perchlorates, N-bromosuccinimide, N-bromoacetamide or potassium ferrates; reducing agents such as dihydrogen in the presence of a Pd or Pt catalyst; electrophiles such as maleimide, nitrobenzene, nitroolefins or quinones such as naphthoquinones, for example (U.S. Pat. No. 7,544,794; WO2020/165334: US2021/214382). Currently, this step is mostly performed by means of sodium nitrite, which has however been found to alter the structure of nucleobases, especially to favor oxidative deamination of adenine, guanine and cytosine (Hutter et al., 2010); US20180066295A1—Deamination of Organophosphorus-Nucleosides). These structural alterations result in mutations which limit the practical utility of the 3'-O-amino protecting group, notably in 3'-$ONH_2$-NTPs-based enzymatic DNA synthesis for biology applications. Sodium nitrite is also unstable in aqueous medium even under slightly acidic pH, thus releasing nitrogen dioxide over time. It may also cause damages to residual polymerase protein. A solution to decrease these side effects of sodium nitrite has been proposed in U.S. Pat. No. 11,505,815, which consists of using an azide-masked nitrogenous heterocycle in enzymatic DNA synthesis.

In view of the interest in extending the application of enzymatic synthesis of polynucleotides or sequencing applications, it would be desirable to provide a simple solution in order to overcome the above problems and in particular which afford deprotecting the oligonucleotide under conditions sufficiently mild to leave the nucleobases intact and thus provide higher polynucleotide purity/better accuracy of DNA/RNA sequencing. These deprotecting agents should also provide cleavage of the protected elongated polynucleotide with high yield to allow the incorporation of the next nucleotide to proceed.

α-carbonylphosphonates have been known for their ability to cleave O—$NH_2$ functions (Khomich, O. et al. 2017. "On the Reaction of Carbonyl Diphosphonic Acid with Hydroxylamine and O-Alkylhydroxylamines: Unexpected Degradation of P-C-P Bridge." *Molecules* 2017. Vol. 22. Page 1040 22(7):1040). However, to the best of the Applicant's knowledge, they have never been used in the deprotection of polynucleotides, all the more so for overcoming the above deficiencies of other deprotecting agents such as sodium nitrite.

SUMMARY OF THE DISCLOSURE

In this context, the inventors have found that specific phosphonate compounds allow overcoming the above problem, since they have no visible activity towards deamination, oxidation, depurination and other non-desired reactions either with nucleosides, oligodeoxynucleotides or fluorescent/non-fluorescent tags. In addition, they can be used under conditions sufficiently mild, on the one hand, to leave the nucleobases intact and thus provide higher polynucleotide purity/better accuracy of DNA/RNA sequences and, on the other hand, to keep the same polymerase during several cycles. The inventors have also shown that these compounds even provide for higher cleavage yield than sodium nitrite.

This disclosure is thus directed to a method of synthesizing a polynucleotide, the method comprising the steps of:
(a) providing initiators which are polynucleotides having each a free 3'-hydroxyl;
(b) repeating in a reaction mixture, until the polynucleotide is formed, cycles of (i) contacting under elongation conditions the initiators or elongated fragments having free 3'-hydroxyls with a 3'-O—$NH_2$ nucleoside triphosphate and a polymerase, so that the initiators or elongated fragments are elongated by incorporation of a 3'-O-amino nucleoside triphosphate to form 3'-O-amino elongated fragments, and (ii) deprotecting the elongated fragments to form elongated fragments having free 3'-hydroxyls, wherein deprotecting is performed by contacting the elongated fragments with an effective amount of at least one phosphonate compound having the following formula (I):

$$R-P(=O)(OM)OM \qquad (I)$$

in which:
 each M is independently selected from the group consisting of: H; a monovalent or divalent metal atom; $HNR^6_3+$ or $NR^6_4+$ wherein each $R^6$ independently designates H or a linear or branched alkyl group having from 1 to 6 carbon atoms; a protonated organic base: a linear or branched alkyl group having from 1 to 6 carbon atoms; aryl; and a $Si(R_4)_3$ group wherein each $R_4$ is independently selected from an aryl group and a linear or branched alkyl group having from 1 to 6 carbon atoms;
 R is $-CO-R_1$ wherein $R_1$ is selected from: (i) a linear or branched alkyl group having from 1 to 6 carbon atoms, (ii) an aryl group and (iii) a $-P(=O)(OM)OM$ group.

In a preferred embodiment, the at least one phosphonate compound is:

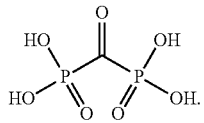

This disclosure also pertains to a kit for synthesizing a polynucleotide, comprising a vial of a polymerase and an effective amount of a phosphonate compound of formula (I).

It further relates to a method for deprotecting 3'-O-amino elongated fragments of a polynucleotide in a method of synthesizing a polynucleotide, comprising contacting the elongated fragments with at least one phosphonate compound of formula (I).

This disclosure also relates to a method for preparing a compound of formula (I) which is a carbonylbisphosphonate salt, comprising the following steps:
1) mixing tetraalkyl methylenediphosphonate with a sodium hydrochlorite solution at room temperature until a first precipitate has formed,
2) recovering the precipitate and dissolving it in a boiling halogenated organic solvent (such as dichlorobenzene or tetrachloroethylene) to obtain a mixture,
3) adding this mixture stepwise into a reactor and refluxing the content of the reactor, thus resulting in propene gas evolvement and the formation of a second precipitate comprising dihalomethylene diphosphonate,
4) cooling down the reactor and recovering said second precipitate,
5) mixing said precipitate with an aqueous solution of an inorganic base and refluxing until to obtaining a third precipitate, and
6) cooling down this mixture and recovering said third precipitate, which comprises a carbonylbisphosphonate salt.

Other embodiments are also disclosed herein as will be apparent to those of ordinary skill in the art from this disclosure including but not limited to the drawings.

BRIEF DESCRIPTION OF THE DRAWINGS

FIG. 4A shows HPLC profiles of dTTP-$ONH_2$ treated with sodium nitrite followed by quenching with acetone: A. with 2 eq, B. 10 eq and C. 50 eq, under the following conditions: 1. pH 5.0/incubation 5 min, 2. pH 6.0/incubation 5 min, 3. pH 5.0/incubation 20 min, 4. pH 6.0/incubation 20 min, 5. pH 5.0/incubation 60 min, 6. pH 6.0/incubation 60 min.

FIG. 4B shows HPLC profiles of dTTP-$ONH_2$ treated with 2 eq. tetrasodium carbonylbisphosphonate followed by quenching with acetone under the following conditions: 1-4: incubation 5 min/pH=5, 6, 7, 8:5-8: incubation 20 min/pH=5, 6, 7, 8:9-12: incubation 60 min/pH=5, 6, 7, 8.

DETAILED DESCRIPTION OF THE DISCLOSURE

Definitions

Figure 1:
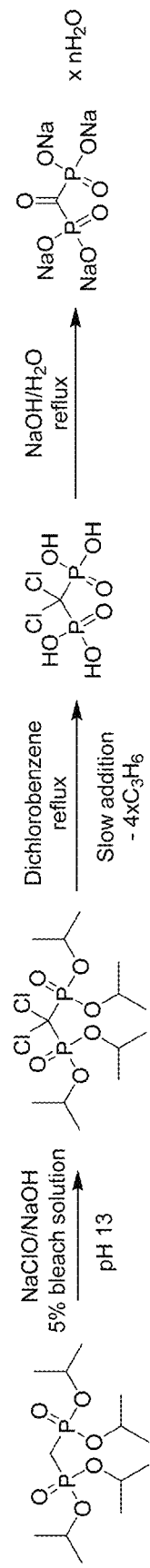
FIG. 1 shows the reaction scheme used to prepare tetrapotassium carbonylbisphosphonate—a deprotecting agent according to this disclosure.

Although polynucleotides typically have at least 100 nucleotide units, "polynucleotide" or "oligonucleotide" are used interchangeably in this description and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Unless otherwise noted the terminology and atom numbering conventions will follow those disclosed in Strachan and Read, Human Molecular Genetics 2 (Wiley-Liss, New York, 1999). Thus, "A" denotes deoxyadenosine, "C" denotes deoxycytidine, "G" denotes deoxyguanosine, and "T" denotes thymidine, "I" denotes deoxyinosine, "U" denotes uridine. Usually polynucleotides comprise the four natural nucleosides (e.g. deoxyadenosine, deoxycytidine, deoxyguanosine, deoxythymidine for DNA or their ribose counterparts for RNA) linked by phosphodiester linkages: however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

The term "alkyl" refers to a saturated, linear or branched aliphatic group such as methyl, ethyl, propyl, isopropyl, butyl, isobutyl, tert-butyl, pentyl, or hexyl.

The term "aryl" corresponds to a mono- or bi-cyclic aromatic hydrocarbon such as phenyl, biphenyl, or naphthyl, preferably phenyl.

Alkyl and aryl groups as defined above also include the corresponding mono- or poly-substituted groups (e.g., in a preferred embodiment resulting in O-hydroxybenzoyl). Examples of substituents include, but are not limited to, $(C_1-C_6)$alkyl, $(C_3-C_{12})$cycloalkyl, $(C_6-C_{14})$aryl, F, Cl, Br, I, CN, $NO_2$, $CF_3$, $R^7O$— (in a preferred embodiment $R^7$ can be H, yielding the substituent HO—), $R^8S$—, $R^9NH$— and $R^{10}R^{11}N$—, $R^7$, $R^8$, $R^9$, $R^{10}$ and $R^{11}$ being each independently selected from $(C_1-C_6)$alkyl, $(C_3-C_{12})$cycloalkyl and $(C_6-C_{14})$aryl.

As mentioned above, the method of the disclosure for synthesizing a polynucleotide comprises the steps of:
(a) providing initiators which are polynucleotides having each a free 3'-hydroxyl;
(b) repeating in a reaction mixture, until the polynucleotide is formed, cycles of (i) contacting under elongation conditions the initiators or elongated fragments having free 3'-hydroxyls with a 3'-O—$NH_2$ nucleoside triphosphate and a polymerase so that the initiators or elongated fragments are elongated by incorporation of a 3'-O-amino nucleoside triphosphate to form 3'-O-amino elongated fragments, and (ii) deprotecting the elongated fragments to form elongated fragments having free 3'-hydroxyls.

This method is characterized in that a specific type of deprotecting agent is used, namely at least one phosphonate compound having the following formula (I):

$$R-P(=O)(OM)OM \qquad (I)$$

in which:
each M is independently selected from the group consisting of: H: a monovalent or divalent metal atom; $HNR^6_3{}^+$ or $NR^6_4{}^+$ wherein each $R^6$ independently designates H or a linear or branched alkyl group having from 1 to 6 carbon atoms (such as tetramethylammonium or tetraethylammonium); a protonated organic base; a linear or branched alkyl group having from 1 to 6 carbon atoms; aryl; and a $Si(R_4)_3$ group wherein each $R_4$ is independently selected from an aryl group and a linear or branched alkyl group having from 1 to 6 carbon atoms;
R is —CO—$R_1$ wherein $R_1$ is selected from: (i) a linear or branched alkyl group having from 1 to 6 carbon atoms, (ii) an aryl group and (iii) a —P(=O)(OM)OM group.

According to a preferred embodiment, the phosphonate compound of formula (I) is such that $R_1$ is selected from a linear or branched alkyl group having from 1 to 6 carbon atoms and a —P(=O)(OM)OM group, preferably $R_1$ is a —P(=O)(OM) OM group.

According to a preferred embodiment, M is selected from: H, a monovalent or divalent metal atom such as Li, Na, K, Cs, Ca, Mg, Cu and Zn and a protonated organic base, preferably M is selected from an alkali metal, such as sodium, lithium or potassium, and an organic base, such as pyridine, N-methylpyridine, dimethylaminopyridine, aniline, dimethylaniline, imidazole, N-methylimidazole, diisopropylethylamine, diisopropylamine or triethylamine.

Still preferably, the phosphonate compound of formula (I) is such that $R_1$ is a —P(=O)(OM)OM group and M is H or an alkali metal, preferably sodium or potassium. These compounds will be referred to in this description as carbonylbisphosphonate and its salts.

In another embodiment, the phosphonate compound of formula (I) is such that $R_1$ is methyl and M is H.

In still another embodiment, the phosphonate compound of formula (I) is such that $R_1$ is n-hexyl and M is H.

Examples of other phosphonate compounds of formula (I) are provided below:

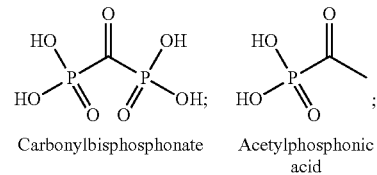

Carbonylbisphosphonate     Acetylphosphonic acid

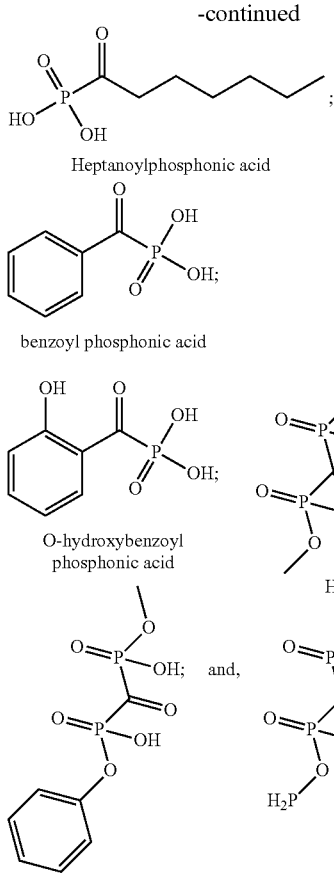

Heptanoylphosphonic acid benzoyl phosphonic acid

O-hydroxybenzoyl
phosphonic acid

The deprotecting agent is used in this disclosure in an effective amount. As used herein, the term an "effective amount" means an amount or concentration sufficient to cleave a 3'-$ONH_2$ polynucleotide when contacted with the latter. It is understood that one of ordinary skill could readily determine an effective amount of the deprotecting agent by conventional techniques, as provided in the Examples. In some embodiments, e.g., employing carbonylphosphonate and its salts as deprotecting agents, an effective amount is provided by a concentration in the range of from 0.1 to 500 mM, or in other embodiments in the range of from 0.1 to 200 mM, or in other embodiments in the range of from 0.1 to 100 mM. Stated otherwise, the molar ratio between the polynucleotides and the deprotecting agent typically ranges from 1:1 to 1:1000 and preferably from 1:1 to 1:100.

The deprotecting agent is typically provided in an aqueous solution buffered at a pH of from 4 to 8, preferably from 5 to 7 (i.e. buffer), wherein the buffering agent may be selected from citrates, phosphates such as sodium phosphate, acetates such as sodium acetate or bicarbonates. As shown in the Examples, some of the deprotecting agents of this disclosure are more effective at a pH around 5, such as carbonylbisphosphonate, while others are more effective at a pH around 8, like heptanoylphosphonic acid. The skilled person will be able to select the appropriate deprotecting agent depending on the intended pH of the synthesis.

According to a preferred embodiment of this disclosure, the buffer may further include at least one inorganic salt of a divalent metal such as magnesium, calcium, zinc or copper, preferably magnesium sulfate, which has been found to increase the cleavage yield, especially at higher pH. This compound may be comprised within the buffer in an amount ranging from 1 to 100 equivalents, preferably from 1 to 10 equivalents, with respect to the compound of formula (I).

In addition to water, the buffer may further include at least one organic solvent which is miscible with water, especially a polar protic solvent, such as methanol or ethanol (up to about 50% v/v), or a polar aprotic solvent, such as tetrahydrofuran or dioxane (up to about 40% v/v). Alternatively or in addition to these organic solvents, the buffer may also include one or more denaturants, such as formamide, urea, dimethylformamide or dimethylsulfoxide (up to about 25%).

The synthesis of tetrasodium salt of carbonylbisphosphonate is described in the literature (Khomich, O. A.; Yanvarev, D. V.; Novikov, R. A.; Kornev, A. B.; Puljulla, E.; Vepsäläinen, J.; Khomutov, A. R.; Kochetkov, S. N. On the Reaction of Carbonyl Diphosphonic Acid with Hydroxylamine and O-Alkylhydroxylamines: Unexpected Degradation of P-C-P Bridge. *Molecules* 2017. Vol. 22. Page 1040 2017, 22 (7), 1040).

The inventors have found that this compound may be obtained by various means starting from tetraisopropyl (dichloromethylene)bis(phosphonate) which may itself be prepared as taught by Quimby, O. T.; Prentice, J. B.; Nicholson, D. A. Tetrasodium Carbonyldiphosphonate. Synthesis, Reactions, and Spectral Properties. *Journal of Organic Chemistry* 1967, 32 (12), 4111-4114. In a first step, this compound may be hydrolysed in presence of TMSBr in dioxane or by continuous heating with 18% aqueous hydrochloric acid (Purdie, M. Process for Preparing Methylene Bisphosphonic and Salts. U.S. Pat. No. 6,657,076B1. Sep. 11, 2000). However, both these procedures are time consuming and require aggressive corrosive reagents. Quantitative deesterification may be achieved more easily by pyrolysis of the solid tetraisopropyl derivative at a temperature above 200° C. to obtain dichloromethylene bisphosphonic acid. For better safety, percussion deesterification might be performed in boiling tetrachloroethane as described by Quimby, O. T. (see above). The inventors have found that this step may be performed even faster in an halogenated organic solvent such as dichlorobenzene by adding of small portions of tetraisopropyl ester to the boiling solution. The pyrolysis step is exothermic and auto-catalyzed by formed bisphosphonic acid leading to instant gas evolving. Accordingly, loading of the reactor with the starting ester has to be done slowly portion wise. Basic hydrolysis of dichloromethylene derivative may then be performed by refluxing with aqueous solution of sodium hydroxide.

Of course, as similar strategy may be followed to prepare other carbonylbisphophonate salts, by changing the base used in the last step by other organic or inorganic bases such as triethylamine, pyridine or potassium hydroxide. It may further be extended to starting materials bearing other alkyl groups than isopropyl groups.

In addition, non-symmetrical carbonylphosphonates bearing different substituents may generally be prepared by Arbuzov reaction between RC(O)Cl and $P(OR^1)_3$ to obtain $RC(O)P(O)(OR^1)_2$ followed by acidic or basic hydrolysis depending on $R^1$. Examples of synthesis routes are provided by Z. Y. Peng et al., *Biochemical Pharmacology*, Vol. 49, No. 1, 105-113 (1995); R. Karaman et al., *J. Chem. Soc. Perkin Trans.* 1, 765-774 (1989); C. E. McKENNA et al., *J. Chem. Soc. Chem. Commun.*, 246-247 (1989). These experimental conditions may of course be optimized by the skilled artisan.

The method for preparing a compound of formula (I) which is a carbonylbisphosphonate salt according to this disclosure thus comprises the following steps:

1) mixing tetraalkyl methylenediphosphonate with a sodium hypochlorite solution at room temperature until a first precipitate has formed,
2) recovering the precipitate and dissolving it in a boiling halogenated organic solvent (such as dichlorobenzene or tetrachloroethylene) to obtain a mixture,
3) adding this mixture stepwise into a reactor and refluxing the content of the reactor, thus resulting in propene gas evolvement and the formation of a second precipitate comprising dihalomethylene diphosphonate,
4) cooling down the reactor and recovering said second precipitate,
5) mixing said precipitate with an aqueous solution of an inorganic base and refluxing until obtaining a third precipitate, and
6) cooling down this mixture and recovering said third precipitate, which comprises a carbonylbisphosphonate salt.

According to an embodiment, the inorganic base used in step (5) is sodium hydroxide. In this embodiment, the process may include a further step of substituting the sodium ions of the carbonylbisphosphonate salt with a protonated organic base. This further step allows improving the solubility of the deprotecting agent. In another embodiment, the inorganic base used in step (5) is potassium hydroxide. In this embodiment, no ion exchange is necessary, although the potassium ions of the carbonylbisphosphonate salt may be substituted with a protonated organic base if desired. It was shown that the deprotecting agent in the form of a potassium salt thus obtained had a high solubility and provided for increased yield and purity. In these ion exchange steps, which may be carried out under conditions easily adjustable by the skilled artisan, the organic base may be selected from: pyridine, N-methylpyridine, dimethylaminopyridine, aniline, dimethylaniline, imidazole, N-methylimidazole, diisopropylethylamine, diisopropylamine and triethylamine, preferably N-methylimidazole.

The deprotecting agent described above is used in a method for synthesizing polynucleotides.

According to a first aspect of this disclosure, the polymerase used in this method is a template-independent polymerase. The method of this disclosure is then preferably an enzymatic DNA synthesis or an enzymatic RNA synthesis.

These methods comprise repeated cycles of steps (illustrated in FIG. 2) in which a predetermined 3'-O-protected nucleotide is (i) coupled to an initiator or growing chain in each cycle and (ii) deprotected. The general elements of template-free enzymatic synthesis of polynucleotides are described in the following references: Champion et al, WO2019/135007: Hiatt et al, U.S. Pat. No. 5,763,594; and Jensen et al, Biochemistry, 57:1821-1832 (2018). 3'-O—$NH_2$ nucleoside triphosphates which may be used as 3'-O-protected nucleotides in this process may be obtained as described, for instance, in WO2020/165334 or WO2021/198040.

In another aspect of this disclosure, the polymerase is a template-dependent polymerase. The method of this disclosure is then preferably a method for sequencing DNA by synthesis, for example, sequencing-by-synthesis (SBS) and sequencing-by-binding (SBB).

According to an embodiment, the sequencing-by-synthesis method comprises the steps of:
(a) providing initiators which are polynucleotides having each a free 3'-hydroxyl;
(b) repeating in a reaction mixture, until the polynucleotide is formed, cycles of:
(i) contacting under elongation conditions the initiators or elongated fragments having free 3'-hydroxyls with a fluorescently labelled 3'-O—$NH_2$ nucleotide and a polymerase, so that the initiators or elongated fragments are elongated by incorporation of a fluorescently labelled 3'-O-amino nucleotide to form 3'-O-amino elongated fragments,
(ii) washing away excess of non-incorporated nucleotides,
(iii) reading the fluorescence signal to know the nucleotide incorporated,
(iv) removing the fluorescent label and removing 3'-O-amino group to form elongated fragments having free 3'-hydroxyls by means of the phosphonate compound of formula (I), and
(v) repeating steps (i) to (iv) until the end of sequencing.

According to an embodiment, the sequencing-by-binding method comprises the steps of:
(a) providing initiators which are polynucleotides having each a free 3'-hydroxyl;
(b) repeating in a reaction mixture, until the polynucleotide is formed, cycles of:
(i) contacting under elongation conditions the initiators or elongated fragments having free 3'-hydroxyls with a 3'-O—$NH_2$ nucleotide and a polymerase, so that the initiators or elongated fragments are elongated by incorporation of 3'-O-amino nucleotide to form 3'-O-amino elongated fragments,
(ii) contacting under elongation conditions the 3'-O-amino elongated fragments with a fluorescently labelled nucleotide and a polymerase, so that the fluorescently labelled nucleotide is bound in the active site of the polymerase,
(iii) washing away unbound fluorescently labelled nucleotides,
(iv) reading the fluorescence signal to know the nucleotides bound in the active site,
(v) washing away the bound nucleotides,
(vi) deprotecting the 3'-O—$NH_2$ polynucleotide with the phosphonate compound of formula (I), and
(vii) repeating steps (i) to (vi) until the end of sequencing.

Figure 2:
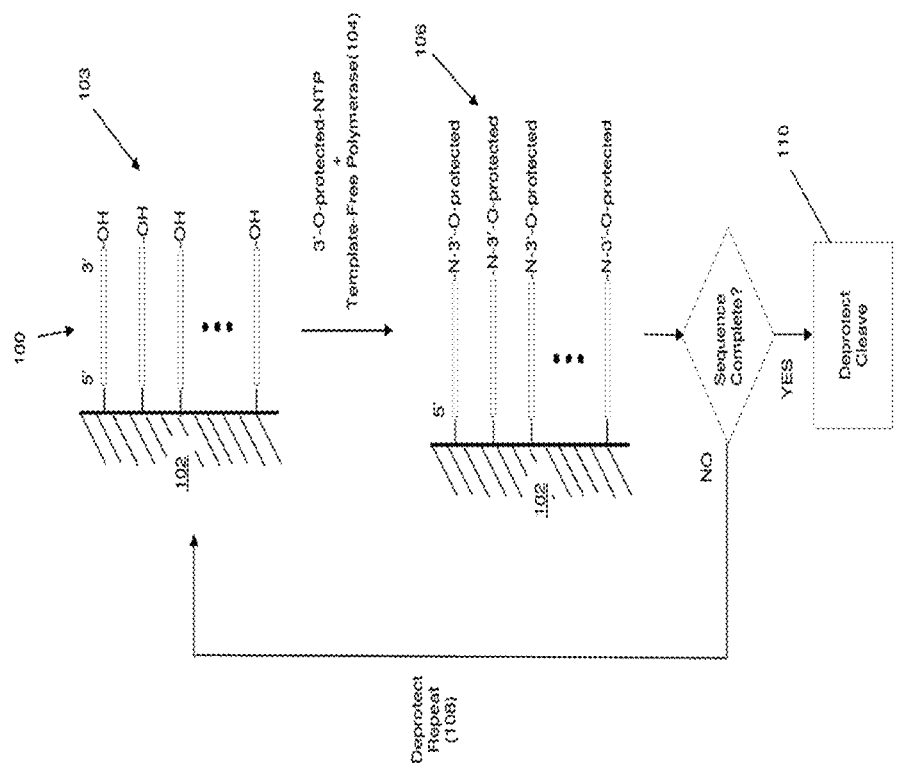
FIG. 2 illustrates the steps of the template-free enzymatic method of synthesizing a polynucleotide according to this disclosure.

A specific embodiment of the process for synthesizing polynucleotides according to this disclosure will now be described with reference to FIG. 2.

Initiator polynucleotides (100) are provided, for example, attached to solid support (102), which have free 3'-hydroxyl groups (103). To the initiator polynucleotides (100) (or elongated initiator polynucleotides in subsequent cycles) are added a 3'-O-protected-dNTP or 3'-O-protected-rNTP and a polymerase, such as a TdT or variant thereof usually for DNA synthesis (e.g. Ybert et al, WO/2017/216472: Champion et al, WO2019/135007) or a poly A polymerase (PAP) or poly U polymerase (PUP) or variant thereof usually for RNA synthesis (e.g. Heinisch et al, WO2021/018919) under conditions effective for the enzymatic incorporation of the 3'-O-protected-NTP onto the 3' end of the initiator polynucleotides (100) (or elongated initiator polynucleotides). This reaction produces elongated initiator polynucleotides whose 3'-hydroxyls are protected (106).

If the elongated sequence is not complete, then another cycle of addition is implemented (108). The 3'-O-protection groups are removed by the deprotecting agent of this disclosure to expose free 3'-hydroxyls (103) and the elongated initiator polynucleotides are subjected to another cycle of nucleotide addition and deprotection.

If the elongated initiator polynucleotide contains a completed sequence, then the 3'-O-protection group may be removed, or deprotected, and the desired sequence may be cleaved from the original initiator polynucleotide (110). Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase.

As used herein, the term "protected" in reference to specified groups, such as a 3'-hydroxyl of a nucleotide or a nucleoside is intended to mean a moiety which is attached covalently to the specified group that prevents a chemical change to the group during a chemical or enzymatic process. Whenever the specified group is a 3'-hydroxyl of a nucleoside triphosphate, or an extended fragment in which a 3'-protected (or blocked)-nucleoside triphosphate has been incorporated, the prevented chemical change is a further, or subsequent, extension of the extended fragment by an enzymatic coupling reaction.

As used herein, an "initiator" refers to a short oligonucleotide sequence with a free 3'-hydroxyl at its end, which can be further elongated by a polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20) nucleotides. In some embodiments, the initiating fragment is single-stranded. In alternative embodiments, the initiating fragment may be double-stranded. In some embodiments, an initiator oligonucleotide may be attached to a synthesis support by its 5' end; and in other embodiments, an initiator oligonucleotide may be attached indirectly to a synthesis support by forming a duplex with a complementary oligonucleotide that is directly attached to the synthesis support, e.g., through a covalent bond. In some embodiments a synthesis support is a solid support which may be a discrete region of a planar solid, or may be a bead.

In some embodiments, an initiator may comprise a non-nucleic acid compound having a free hydroxyl to which a TdT may couple a 3'-O-protected dNTP. e.g. Baiga. U.S. patent publications US2019/0078065 and US2019/0078126.

Synthesis supports to which initiators are attached may comprise polymers, porous or non-porous solids, including beads or microspheres, planar surfaces, such as a glass slide, membrane, or the like. In some embodiments, a solid support, or synthesis support, may comprise magnetic beads, particle-based resins, such as agarose, or the like.

Synthesis supports include, but are not limited to, soluble supports, such as, polymer supports, including polyethylene glycol (PEG) supports, dendrimer supports and the like; non-swellable solid supports, such as, polystyrene particles; swellable solid supports, such as resins or gels, including agarose. Synthesis supports may also form part of reaction chambers, such as, the filter membrane of a filter plate. Guidance for selecting soluble supports is found in references Bonora et al, Nucleic Acids Research, 212(5): 1213-1217 (1993); Dickerson et al, Chem. Rev. 102:3325-3344 (2002); Fishman et al, J. Org. Chem., 68:9843-9846 (2003); Gavert et al, Chem. Rev. 97:489-509 (1997); Shchepinov et al, Nucleic Acids Research, 25(22): 4447-4454 (1997); and like references. Guidance for selecting solid supports is found in Brown et al, Synlett 1998(8): 817-827; Maeta et al, U.S. Pat. No. 9,045,573: Beaucage and Iyer, Tetrahedron, 48(12): 2223-2311 (1992); and the like. Guidance for attaching oligonucleotides to solid supports is found in Arndt-Jovin et al. Eur. J. Biochem., 54:411-418 (1975); Ghosh et al, Nucleic Acids Research, 15(13): 5353-5372 (1987); Integrated DNA Technologies, "Strategies for attaching oligonucleotides to solid supports." 2014 (v6); Gokmen et al, Progress in Polymer Science 37:365-405 (2012); and like references.

In some embodiments, the solid-phase support will typically be comprised of porous beads or particles in the form of a resin or gel. Numerous materials are suitable as solid-phase supports for the synthesis of polynucleotides. As used herein, the term "particle" includes, without limitation, a "microparticle" or "nanoparticle" or "bead" or "microbead" or "microsphere."

In some embodiments, a porous resin support derivatized with initiators has average pore diameters of at least 10 nm, or at least 20 nm, or at least 50 nm. In other embodiments, such porous resin support has an average pore diameter in the range of from 10 nm to 500 nm, or in the range of from 50 nm to 500 nm.

In some embodiments, initiators are attached to planar supports for massively parallel synthesis of oligonucleotides, e.g. via inkjet delivery of reagents, such as described by Horgan et al, International patent publication WO2020/020608, which is incorporated herein by reference. In some embodiments such planar supports comprise a uniform coating of initiators with protected 3'-hydroxyls, wherein, for example, discrete reaction sites may be defined by delivering deprotection solution to discrete locations. In other embodiments, such planar supports comprise an array of discrete reaction sites each containing initiators, which, for example, may be formed on a substrate by photolithographic methods of Brennan, U.S. Pat. No. 5,474,796; Peck et al, U.S. Pat. No. 10,384,189; Indermuhle et al, U.S. Pat. No. 10,669,304; Fixe et al, Materials Research Society Symposium Proceedings. Volume 723, Molecularly Imprinted Materials—Sensors and Other Devices. Symposia (San Francisco, California on Apr. 2-5, 2002); or like references.

After synthesis is completed polynucleotides with the desired nucleotide sequence may be released from initiators and the solid supports by cleavage. A wide variety of cleavable linkages or cleavable nucleotides may be used for this purpose. In some embodiments, cleaving the desired polynucleotide leaves a natural free 5'-hydroxyl on a cleaved strand; however, in alternative embodiments, a cleaving step may leave a moiety, e.g. a 5'-phosphate, that may be removed in a subsequent step, e.g. by phosphatase treatment. Cleaving steps may be carried out chemically, thermally, enzymatically or by photochemical methods. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage may be accomplished by providing initiators with a deoxyinosine as the penultimate 3' nucleotide, which may be cleaved by endonuclease V at the 3' end of the initiator leaving a 5'-phosphate on the released polynucleotide, e.g. as taught by Creton, International patent publication WO2020/165137. Returning to FIG. 2, in some embodiments, an ordered sequence of nucleotides are coupled to an initiator nucleic acid using a polymerase, such as TdT, in the presence of 3'-O-protected NTPs in each synthesis step. The above method may also include a washing step after each reaction, or extension, step, as well as after each de-protecting step.

When the sequence of polynucleotides on a synthesis support includes reverse complementary subsequences, secondary intra-molecular or cross-molecular structures may be created by the formation of hydrogen bonds between the reverse complementary regions. In some embodiments, base protecting moieties for exocyclic amines are selected so that hydrogens of the protected nitrogen cannot participate in hydrogen bonding, thereby preventing the formation of such secondary structures. That is, base protecting moieties may be employed to prevent the formation of hydrogen bonds, such as are formed in normal base pairing, for example, between nucleosides A and T and between G and C. At the end of a synthesis, the base protecting moieties may be removed and the polynucleotide product may be cleaved from the solid support, for example, by cleaving it from its initiator.

In addition to providing 3'-O-protected NTP monomers with base protection groups, elongation reactions may be performed at higher temperatures using thermal stable polymerases. For example, a thermal stable template-free polymerase having activity above 40° C. may be employed; or, in some embodiments, a thermal stable template-free polymerase having activity in the range of from 40-85° C. may be employed; or, in some embodiments, a thermal stable template-free polymerase having activity in the range of from 40-65° C. may be employed.

In some embodiments, elongation (or coupling) conditions may include adding solvents to an elongation reaction mixture that inhibit hydrogen bonding or base stacking. Such solvents include water miscible solvents with low dielectric constants, such as dimethyl sulfoxide (DMSO), methanol, and the like. Likewise, in some embodiments, elongation conditions may include the provision of chaotropic agents that include, but are not limited to, n-butanol, ethanol, guanidinium chloride, lithium perchlorate, lithium acetate, magnesium chloride, phenol, 2-propanol, sodium dodecyl sulfate, thiourea, urea, and the like. In some embodiments, elongation conditions include the presence of a secondary-structure-suppressing amount of DMSO. In some embodiments, elongation conditions may include the provision of DNA binding proteins that inhibit the formation of secondary structures, wherein such proteins include, but are not limited to, single-stranded binding proteins, helicases, DNA glycolases, and the like.

3'-O-amino-dNTPs without base protection may be purchased from commercial vendors or synthesized using published techniques, e.g. Benner, U.S. Pat. Nos. 7,544,794 and 8,212,020.

When base-protected dNTPs are employed, the method may further include a step (e) removing base protecting moieties, which in the case of acyl or amidine protection groups may (for example) include treating with concentrated ammonia.

The above method may also include one or more capping steps in addition to washing steps after the coupling (or elongation) step. A first capping step may cap, or render inert to further elongations, unreacted 3'-OH groups on partially synthesized polynucleotides. Such capping step is usually implemented after a coupling step, and whenever a capping compound is used, it is selected to be unreactive with protection groups of the monomer just coupled to the growing strands. In some embodiments, such capping steps may be implemented by coupling (for example, by a second enzymatic coupling step) a capping compound that renders the partially synthesized polynucleotide incapable of further couplings, e.g. with TdT. Such capping compounds may be a dideoxynucleoside triphosphate.

A variety of kits may be provided for implementing the method of this disclosure. In one aspect, kits may comprise one or more containers (or bottles, or vials) of synthesis reagents at least one of which contains an effective amount of a phosphonate compound of formula (I). In some embodiments, kits comprise a vial of polymerase and a vial of an effective amount of at least one phosphonate compound of formula (I).

In some embodiments, kits may include one or more of the following items, either separately or together with the above-mentioned items: (i) one or more containers comprising 3'-O-amino-dNTPs, (ii) solid supports with initiators attached thereto, (iii) cleavage reagents for releasing completed polynucleotides from solid supports, (iv) wash reagents or buffers for removing unreacted 3'-O-amino-dNTPs at the end of an enzymatic addition or coupling step, and (v) post-synthesis processing reagents, such as purification columns, desalting reagents, eluting reagents, and the like.

Items

This description further encompasses the following items:
1. A method of synthesizing a polynucleotide, the method comprising the steps of:
    (a) providing initiators which are polynucleotides having each a free 3'-hydroxyl;
    (b) repeating in a reaction mixture, until the polynucleotide is formed, cycles of (i) contacting under elongation conditions the initiators or elongated fragments having free 3'-hydroxyls with a 3'-O—NH$_2$ nucleoside triphosphate and a polymerase, so that the initiators or elongated fragments are elongated by incorporation of a 3'-O-amino nucleoside triphosphate to form 3'-O-amino elongated fragments, and (ii) deprotecting the elongated fragments to form elongated fragments having free 3'-hydroxyls,
    wherein deprotecting is performed by contacting the elongated fragments with at least one phosphonate compound having the following formula (I):

    R—(=O)(OM)OM                    (I)

in which:
    M is selected from the group consisting of: (a) H, (b) a monovalent or divalent metal atom, (c) HNR$^6_3{}^+$ or NR$^6_4{}^+$ wherein each R$^6$ independently designates H or a linear or branched alkyl group having from 1 to 6 carbon atoms, (d) an organic base, (e) a linear or branched alkyl group having from 1 to 6 carbon atoms; (f) aryl; (g) a Si(R$_4$)$_3$ group wherein each R$_4$ is independently selected from an aryl group or a linear or branched alkyl group having from 1 to 6 carbon atoms; and (h) a PH$_2$ group; and,
    R is selected from the following groups: (a) —CO—R$_1$ wherein R$_1$ is selected from (i) H, (ii) —COOH, (iii) CN, (iv) a linear or branched alkyl group having from 1 to 6 carbon atoms, (v) an aryl group or (vi) a —P(=O)(OMM)OM group; (b) a —C(=CH—R$_2$)—X—R$_3$ group wherein X is O or —NR$^a$R$^b$, wherein R$^a$ and R$^b$ are independently selected from alkyl groups having from 1 to 6 carbon atoms, R$_2$ is a linear or branched alkyl group having from 1 to 6 carbon atoms, R$_3$ is M or a Si(R$_4$)$_3$ group; and (c) a —C(Y)(OH)—R$^5$ group wherein Y is —CN or —SO$_3{}^-$ and R$_5$ is a linear or branched alkyl group having from 1 to 6 carbon atoms.

2. A method of synthesizing a polynucleotide, the method comprising the steps of:
   (a) providing initiators which are polynucleotides having each a free 3'-hydroxyl; and,
   (b) repeating in a reaction mixture, until the polynucleotide is formed, cycles of (i) contacting under elongation conditions the initiators or elongated fragments having free 3'-hydroxyls with a 3'-O—$NH_2$ nucleoside triphosphate and a polymerase, so that the initiators or elongated fragments are elongated by incorporation of a 3'-O-amino nucleoside triphosphate to form 3'-O-amino elongated fragments, and (ii) deprotecting the elongated fragments to form elongated fragments having free 3'-hydroxyls,
   wherein deprotecting is performed by contacting the elongated fragments with an effective amount of at least one phosphonate compound having the following formula (I):

R—P(=)(OM)OM        (I)

in which:
   each M is independently selected from the group consisting of: (a) H, (b) a monovalent or divalent metal atom, (c) $HNR^6_3{}^+$ or $NR^6_4{}^+$ wherein each $R^6$ independently designates H or a linear or branched alkyl group having from 1 to 6 carbon atoms, (d) a protonated organic base, (e) a linear or branched alkyl group having from 1 to 6 carbon atoms, (f) aryl, (g) a $Si(R_4)_4$ group wherein each $R_4$ is independently selected from an aryl group or a linear or branched alkyl group having from 1 to 6 carbon atoms; and (h) a $PH_2$ group; and,
   R is selected from the following groups: (a) —CO—$R_1$ wherein $R_1$ is selected from (i) H, (ii) —COOH, (iii) CN, (iv) a linear or branched alkyl group having from 1 to 6 carbon atoms, (v) an aryl group or (vi) a —P(=O)(OM)OM group; (b) a —C(=CH—$R_2$)—X—$R_3$ group wherein X is O or —$NR^aR^b$, wherein $R^a$ and $R^b$ are independently selected from alkyl groups having from 1 to 6 carbon atoms, $R_2$ is a linear or branched alkyl group having from 1 to 6 carbon atoms, $R_3$ is M or a $Si(R_4)_3$ group; and (c) a —C(Y)(OH)—$R_5$ group wherein Y is —CN or —$SO_3{}^-$ and $R_5$ is a linear or branched alkyl group having from 1 to 6 carbon atoms.

In preferred embodiments, an effective amount of the at least one phosphonate compound is provided by a concentration of said phosphonate compound in the range of from about 0.1 to about 500 mM, optionally about 0.1 to about 100 mM or about 0.1 to about 200 mM, in an aqueous solution buffered at a pH of from about 4 to about 8, optionally from about 5 to about 7.

In preferred embodiments, the at least one phosphonate compound is selected from the group consisting of:

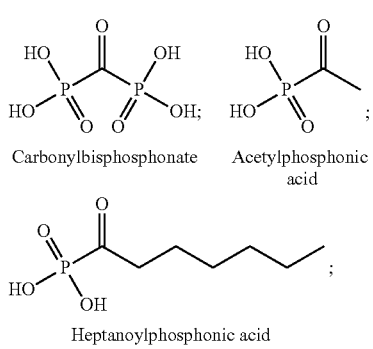

Carbonylbisphosphonate    Acetylphosphonic acid

Heptanoylphosphonic acid

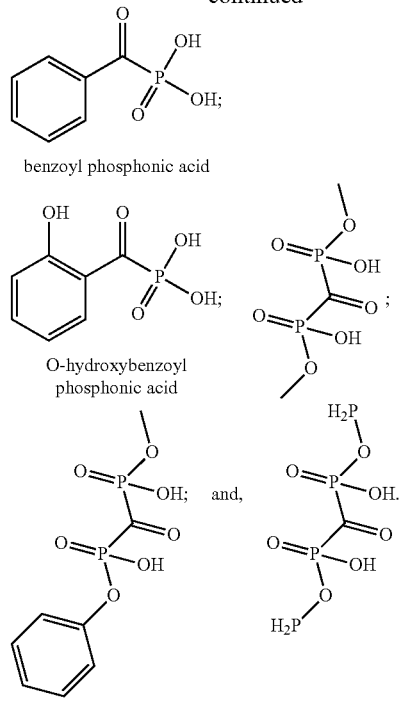

benzoyl phosphonic acid

O-hydroxybenzoyl phosphonic acid

In preferred embodiments, this disclosure relates to the following items:

3. A method of synthesizing a polynucleotide, the method comprising the steps of:
   (a) providing initiators which are polynucleotides having each a free 3'-hydroxyl;
   (b) repeating in a reaction mixture, until the polynucleotide is formed, cycles of:
      (i) contacting under elongation conditions the initiators or elongated fragments having free 3'-hydroxyls with a 3'-O—$NH_2$ nucleoside triphosphate and a polymerase, so that the initiators or elongated fragments are elongated by incorporation of a 3'-O-amino nucleoside triphosphate to form 3'-O-amino elongated fragments, and
      (ii) deprotecting the elongated fragments to form elongated fragments having free 3'-hydroxyls;
   wherein the deprotecting is performed by contacting the elongated fragments with an effective amount of at least one phosphonate compound, wherein at least one phosphonate compound is:

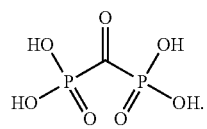

4. The method of item 3, wherein said effective amount is provided by a concentration of said phosphonate compound in the range of from about 0.1 to about 500 mM, optionally about 0.1 to about 100 mM or about 0.1 to about 200 mM, in an aqueous solution buffered at a pH of from about 4 to about 8, optionally from about 5 to about 7.

5. The method of item 4, wherein the aqueous solution comprises at least one inorganic salt of a divalent metal.

6. The method of item 5 wherein the divalent metal is selected from the group consisting of magnesium, calcium, zinc, and copper, optionally wherein the at least one inorganic salt is magnesium sulfate.

7. The method of item 3, wherein the polymerase is a template-independent polymerase.

8. The method of item 7, wherein the template-independent polymerase is Terminal Deoxynucleotidyl Transferase (TdT).

9. The method of item 7, wherein the method is an enzymatic DNA synthesis.

10. The method of item 7, wherein the method is an enzymatic RNA synthesis.

11. The method of item 1, wherein the polymerase is a template-dependent polymerase.

12. The method of item 11, wherein the method is sequencing DNA.

13. The method of item 12, wherein the method is sequencing-by-synthesis (SBS) or sequencing-by-binding (SBB).

14. The method of item 13, wherein the method is sequencing-by-synthesis comprising the steps of:
   (a) providing initiators which are polynucleotides having each a free 3'-hydroxyl;
   (b) repeating in a reaction mixture, until the polynucleotide is formed, cycles of:
      (i) contacting under elongation conditions the initiators or elongated fragments having free 3'-hydroxyls with a fluorescently labelled 3'-O—NH$_2$ nucleotide and a polymerase, so that the initiators or elongated fragments are elongated by incorporation of a fluorescently labelled 3'-O-amino nucleotide to form 3'-O-amino elongated fragments,
      (ii) washing away excess of non-incorporated nucleotides,
      (iii) reading the fluorescence signal to know the nucleotide incorporated,
      (iv) removing the fluorescent label and using the at least one phosphonate compound, preferably at least

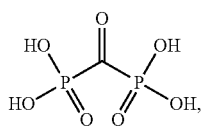

to remove the 3'-O-amino group to form elongated fragments having free 3'-hydroxyls, and
      (v) repeating steps (i) to (iv) until the end of sequencing.

15. The method of item 13, wherein the method is sequencing-by-binding comprising the steps of:
   (a) providing initiators which are polynucleotides having each a free 3'-hydroxyl; and,
   (b) repeating in a reaction mixture, until the polynucleotide is formed, cycles of:
      (i) contacting under elongation conditions the initiators or elongated fragments having free 3'-hydroxyls with a 3'-O—NH$_2$ nucleotide and a polymerase, so that the initiators or elongated fragments are elongated by incorporation of 3'-O-amino nucleotide to form 3'-O-amino elongated fragments,
      (ii) contacting under elongation conditions the 3'-O-amino elongated fragments with a fluorescently labelled nucleotide and a polymerase, so that the fluorescently labelled nucleotide is bound in the active site of the polymerase,
      (iii) washing away unbound fluorescently labelled nucleotides,
      (iv) reading the fluorescence signal to know the nucleotides bound in the active site,
      (v) washing away the bound nucleotides,
      (vi) deprotecting the 3'-O—NH$_2$ polynucleotide with the at least one phosphonate compound, preferably at least

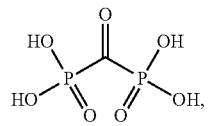

and
      (vii) repeating steps (i) to (vi) until the end of sequencing.

16. A kit for enzymatic synthesis of a polynucleotide, the kit comprising at least one container comprising at least one polymerase and at least one container including at least an effective amount of the phosphonate compound:

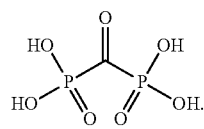

17. The kit of item 16 for using the method of item 1.

18. The kit of item 16 further including instructions for using the method of item 1.

19. A method for deprotecting 3'-O-amino elongated fragments of a polynucleotide in an enzymatic method of synthesizing a polynucleotide, comprising contacting the elongated fragments with at least one phosphonate compound, wherein at least one phosphonate compound is:

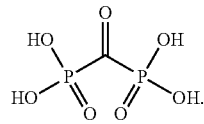

20. A method for preparing the phosphonate compound

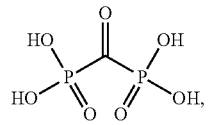

the method comprising the steps of:
   1) mixing tetraalkyl methylenediphosphonate with a sodium hypochlorite solution at room temperature until a first precipitate has formed;
   2) recovering the precipitate and dissolving it in a boiling halogenated organic solvent to obtain a mixture;
   3) adding this mixture stepwise into a reactor and refluxing the content of the reactor, thus resulting in propene gas evolvement and the formation of a second precipitate comprising dichloromethylene diphosphonate, 4) cooling the reactor and recovering said second precipitate,
5) mixing the second precipitate with an aqueous solution of an inorganic base and refluxing to produce a mixture comprising a third precipitate,
6) cooling the mixture of v) and,
7) recovering said third precipitate.

Other embodiments (e.g., items) are also contemplated herein as would be understood by those of ordinary skill in the art from this disclosure.

EXAMPLES

The following examples are put forth so as to provide those of ordinary skill in the art with a complete disclosure and description of how to use the embodiments provided herein and are not intended to limit the scope of the disclosure nor are they intended to represent that the Examples below are all of the experiments or the only experiments performed. Efforts have been made to ensure accuracy with respect to numbers used (e.g., amounts, temperature, etc.) but some experimental errors and deviations should be accounted for. It should be understood that variations in the methods as described can be made without changing the fundamental aspects that the Examples are meant to illustrate.

Example 1: Synthesis of Tetrasodium Carbonylbisphosphonate

NMR spectrum was recorded on 243 MHz (31P) Bruker Avance 600 DRX (Bruker, Karlsruhe, Germany) spectrometer 31P NMR for tetrasodium carbonylbisphosphonate (D2O) δ −0.4 (s, 2P).

Tetraisopropyl(dichloromethylene)bis(phosphonate)

This compound was prepared according to a method similar to that described in Quimby, O. T.; Curry, J. D.; Allan Nicholson, D.; Prentice, J. B.; Roy, C. H. Metalated Methylenediphosphonate Esters. Preparation, Characterization and Synthetic Applications. *J Organomet Chem* 1968, 13 (1), 199-207. Specifically, tetraisopropyl methylenediphosphonate (3.45 g, 10 mmol) was poured into 40 mL of 5 wt % sodium hypochlorite solution (approx. 0.27 mole) at pH 13.0 and stirred at room temperature. The white solid precipitate had been formed in some time and stirring continued for additional 2 h. Then the reaction mixture was filtered off and the precipitate was washed several times with water and dried in air followed by a vacuum desiccator. Tetraisopropyl dichloromethylene diphosphonate was obtained as white solid (4.05 g, 98%) and used in the next step without any further purification. $^1$H NMR (600 MHZ, Chloroform-d) δ 4.94 (dqq, J=9.5, 6.2, 6.2 Hz, 4H), 1.40 (d, J=6.4 Hz, 24H); $^{13}$C NMR (151 MHZ, Chloroform-d) δ 75.29 (t, J=3.6 Hz), 24.47 (s), 23.64 (t, J=3.3 Hz); $^{31}$P NMR (243 MHZ, Chloroform-d) δ 6.71 (s, 2P).

Dichloromethylene Diphosphonate

A round-bottomed flask with a magnetic stirring bar was equipped with a dropping funnel, condenser connected to a bubble counter, and an inlet for nitrogen gas. The reactor was placed into an oil-bath and connected to the cylinder with nitrogen. Tetraisopropyl ester (4.0 g, 9.7 mmol) was dissolved in dichlorobenzene (20 mL) and transferred into a dropping funnel. 1 mL of this mixture and a small portion of dichloromethylene diphosphonic acid was brought up to a boil in the reactor. When the mixture spontaneously decomposed, propene gas released instantly and a grey formed. Afterward the rest mixture was added by drops from the funnel to the reactor upon refluxing and stirring, meanwhile propene gas released through the bubble counter while purging the reactor with nitrogen flow. The addition of tetraisopropyl ester had been completed in 20 min after that refluxing was continued for additional 30 mins. The reactor was removed from the heating bath and cooled down to an ambient temperature and the content was filtered off. The grey precipitate was rinsed on a filter with dichloromethylene several times, transferred to a vacuum desiccator and dried in an oil-pump vacuum to afford 2.21 g (93%) of dichloromethylene diphosphonate as a grey hydroscopic powder. $^1$H NMR (600 MHZ, DMSO-d6) δ 9.47 (s, 4H); $^{13}$C NMR (151 MHZ, DMSO-d6) δ 40.06; $^{31}$P NMR (243 MHZ, DMSO-d6) δ 6.51.

Tetrasodium Carbonylbisphosphonate

Dichloromethylene diphosphonate (2.0 g, 8.8 mmol) was dissolved in deionized water (10 mL) and sodium hydroxide (2.1 g. 53 mmol) was slowly added portion wise. The reaction mixture was stirred upon reflux for 4 h. After cooling down to an ambient temperature, absolute ethanol (20 mL) was added and the formed precipitate was filtered off and washed with abs. ethanol to afford tetrasodium salt carbonylbisphosphonate. The crystalline material had been dried in a vacuum desiccator until constant weight to give a dihydrate of carbonylbisphosphonate (2.4 g, 88%). $^{13}$C NMR (151 MHZ, Deuterium Oxide) δ 244.8 (dd, J=118.8 Hz); $^{31}$P NMR (243 MHZ, Deuterium Oxide) δ −0.43.

Figure 3:
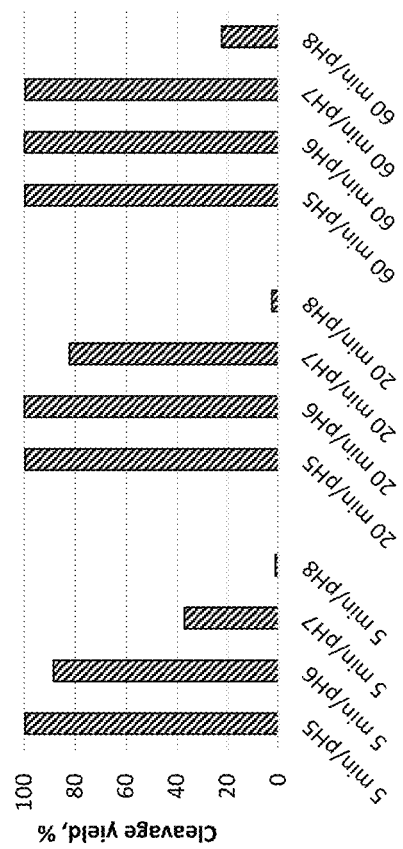
FIG. 3 shows 3'-$ONH_2$ to 3'-OH conversion yield based on the reaction between dTTP-$ONH_2$ and 2 eq of carbonylbisphosphonate at different pHs and reaction times.

Example 2: Deprotection Experiment 1 mM solution of dTTP-3'-ONH$_2$ (100 uL) taken in 50 mM sodium acetate (pH 5.0), 50 mM sodium phosphate (pH 6.0), 50 mM sodium phosphate (pH 7.0) or 50 mM sodium bicarbonate (pH around 8, i.e. 8.25) buffers was agitated with ThermoMixer in sealed Eppendorf tubes with 2 eq of carbonylbisphosphonate as prepared in Example 1, at 25° C. After 5 min/20 min/60 min of incubation the corresponding reaction mixture had been quenched with 5-fold excess of hydroxylamine hydrochloride in 100 uL of deionized water followed by excess of aqueous 5% acetone. Thereby, non-reacted residual dTTP-ONH$_2$ was converted to an inert acetoxime form—dTTP-OX. The quenched reaction mixtures were analyzed with reversed-phase HPLC as shown on FIG. 3 with the following conditions: C18 Xterra 3.5 μm, 4.6×50 mm column (Waters); Buffer A: 50 mM TEAB (pH 8.5), Buffer B: 100% ACN. Gradient elution method: flow rate: 1.5 mL/min, 0-2 min-0% ACN B, 5.3 min-10% ACN, 8 min-30% ACN, 8-10 min-100% ACN. As shown on FIG. 3, after only 5 min at pH 5, conversion of 3'-ONH$_2$ to 3'-OH reaches 100%.

Example 3: Comparative Deprotection Experiment 1 mM solution of dTTP-3'-ONH$_2$ (100 uL) taken in either 50 mM sodium acetate (pH 5.0) or 50 mM sodium phosphate (pH 6.0) buffer was agitated with ThermoMixer in sealed Eppendorf tubes with 2 eq/10 eq/50 eq of sodium nitrite at 25° C. After 5 min/20 min/60 min of incubation the corresponding reaction mixture had been quenched with 100 uL of 5% acetone in 100 mM sodium bicarbonate buffer (pH around 8, i.e. 8.25). Thereby, non-reacted residual dTTP- ONH$_2$ was converted to an inert acetoxime form-dTTP-OX. The quenched reaction mixtures were analyzed with reversed-phase HPLC as shown on FIG. 4 with the following conditions: C18 Xterra 3.5 μm, 4.6×50 mm column (Waters); Buffer A: 50 mM TEAB (pH 8.5), Buffer B: 100% ACN. Gradient elution method: flow rate: 1.5 mL/min, 0-2 min-0% ACN B, 5.3 min-10% ACN, 8 min-30% ACN, 8-10 min-100% ACN.

As shown on FIG. 4A, sodium nitrite reacts several times slower than carbonylbisphosphonate (FIG. 4B) with oxyamines. dTTP-ONH$_2$ being incubated even at pH 5.0/60 mins with 50 eq of sodium nitrite reached only about 80% conversion to dTTP-OH.

Example 4: Deprotection Study with Various Nucleotides

Figure 5:
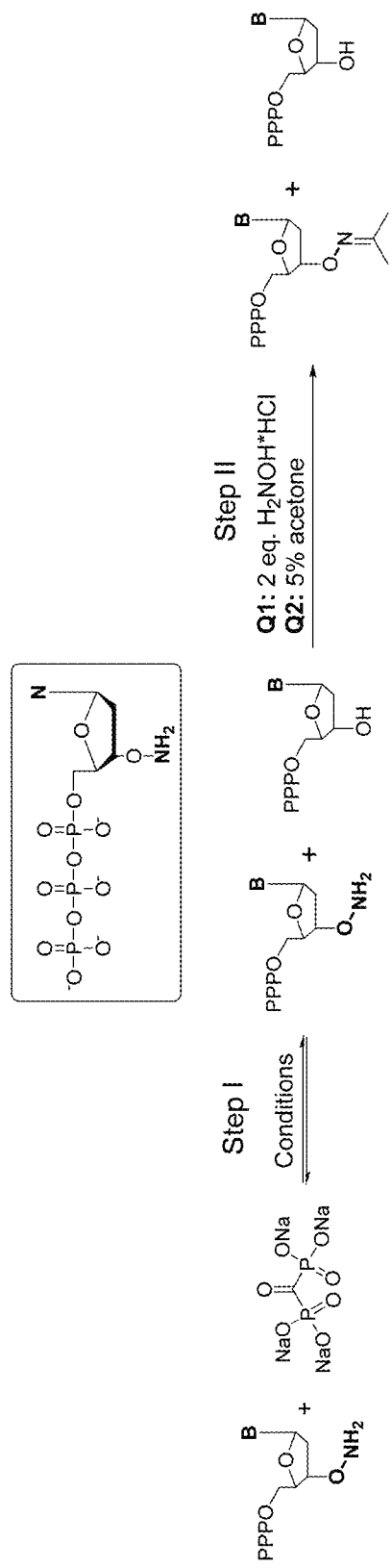
FIG. 5 shows the reaction scheme used in the deprotection study of various 3'-O—$NH_2$ nucleotides with a carbonylbisphosphonate used as a deprotecting agent according to this disclosure.

The general scheme of the reaction conducted in this Example is shown on FIG. 5 (Step I: deprotection; Step II: conversion step prior to HPLC).

Materials and Methods

The screening tests were performed in a 96-well plate with a reaction volume of 100 uL. Nucleoside triphosphate (dATP-3'-ONH$_2$, dTTP-3'-ONH$_2$, dCTP-3'-ONH$_2$ or dGTP-3'-ONH$_2$) were taken at 1 mM final concentration in one of four 50 mM buffers (A: sodium acetate pH 5.0, B: sodium phosphate pH 6.0, C: sodium phosphate 7.0, D: sodium bicarbonate pH around 8, i.e. 8.25). Tetrasodium carbonyl-bisphosphonate was added to the dNTPs solutions at 2 mM final concentration and incubated during 5, 20 or 60 mins prior to quenching with 2× concentration of hydroxylamine hydrochloride. The 96-well plate were agitated with Thermomixer at 25° C. or 40° C. The catalytic effect of magnesium on cleavage rate was also investigated. For this purpose, the same experiments were performed in the presence of 20 mM magnesium sulfate. Prior to HPLC analysis reaction mixtures were additionally quenched with acetone to convert 3'-ONH$_2$ to acetoxime form. The samples were analyzed by RP-HPLC with gradual gradient of acetonitrile in 50 mM TEAB buffer (pH 8.5). The cleavage rate was determined based on the ratio between dNTP-3'-OH and dNTP-3'-acetoxime.

HPLC Conditions

Xterra RP C18 Column: 4.6*50 mm, (3.5 um silica), Buffer A: 50 mM TEAA (pH 7.0), Buffer B: 100% ACN. Method: 0-2 min-0% ACN B, 6 min-10% ACN, 8 min-30% ACN, 8-10 min-100% ACN. Flowrate: 1.5 mL/min, no loop insert.

Results

Figure 6:
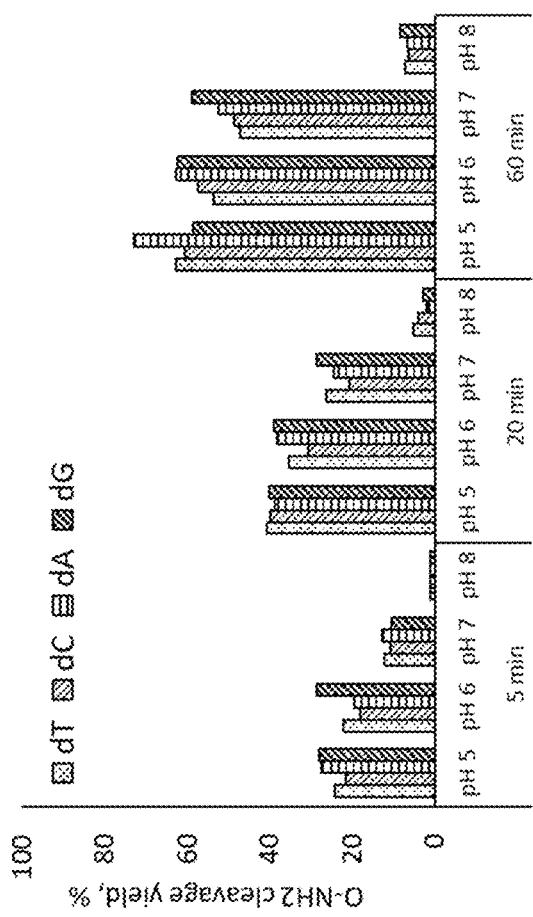
FIG. 6 diagrammatically illustrates the results of the cleavage yield over time for various dNTPs incubated with carbonylbisphosphonate as a deprotecting agent of this disclosure at 25° C., under several pH conditions.
Figure 7:
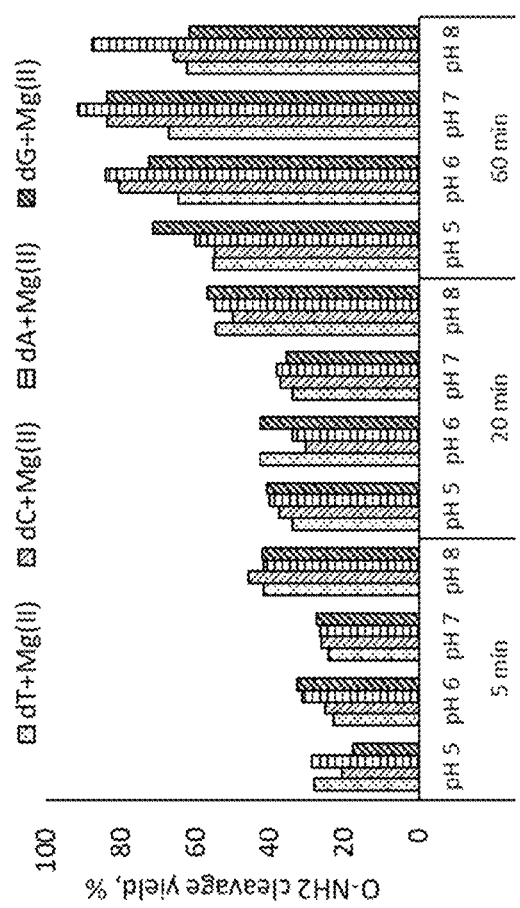
FIG. 7 diagrammatically illustrates the results of the cleavage yield over time for various dNTPs incubated with carbonylbisphosphonate as a deprotecting agent of this disclosure at 25° C., under several pH conditions, in the presence of 20 mM magnesium sulphate.
Figure 8:
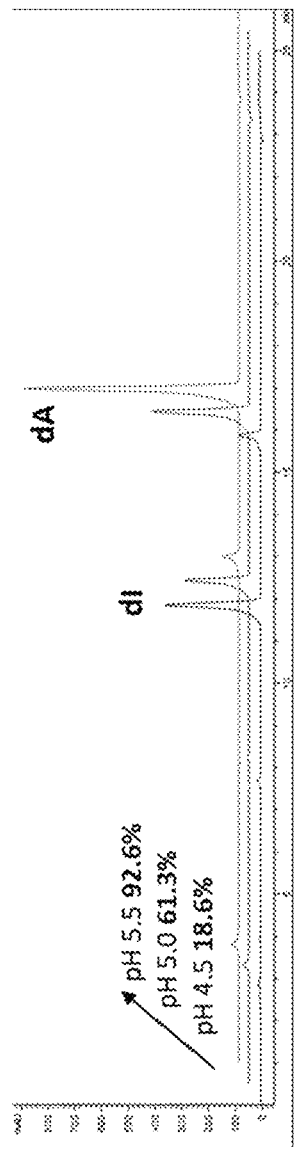
FIGS. 8, 10, 12 and 14 show HPLC profiles for various deoxynucleosides incubated with 0.5M sodium nitrite for 72 h at pH 4.5, 5.0 or 5.5.
Figure 9:
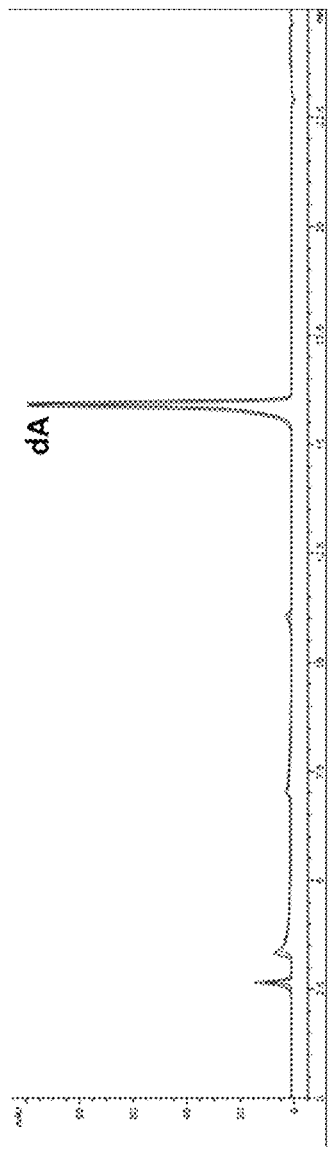
FIGS. 9, 11, 13 and 15 show HPLC profiles for various deoxynucleosides incubated with 0.5M tetrasodium carbonylbisphosphonate for 72 h at pH 4.5, 5.0 or 5.5.
Figure 10:
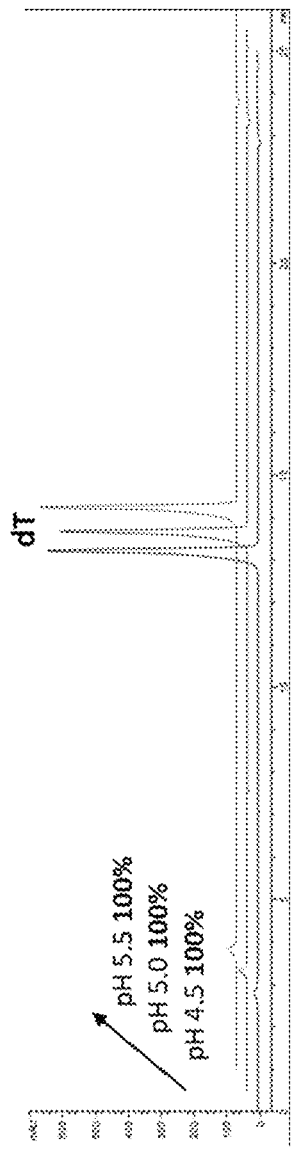
Figure 11:
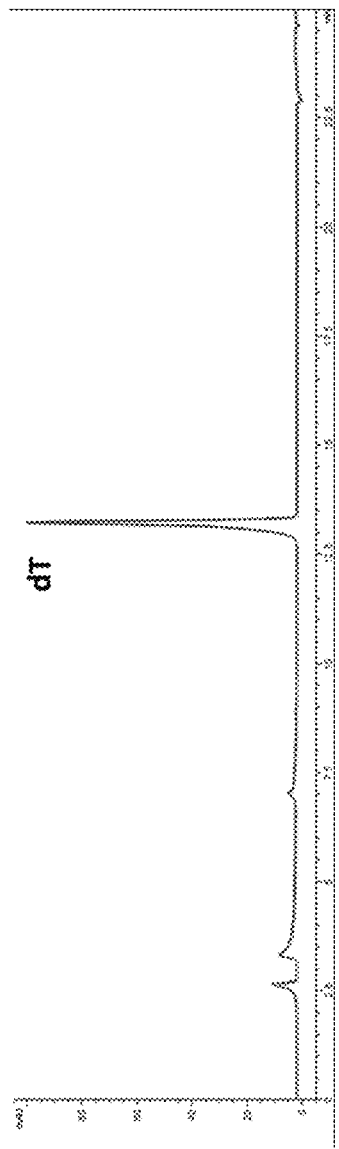
Figure 12:
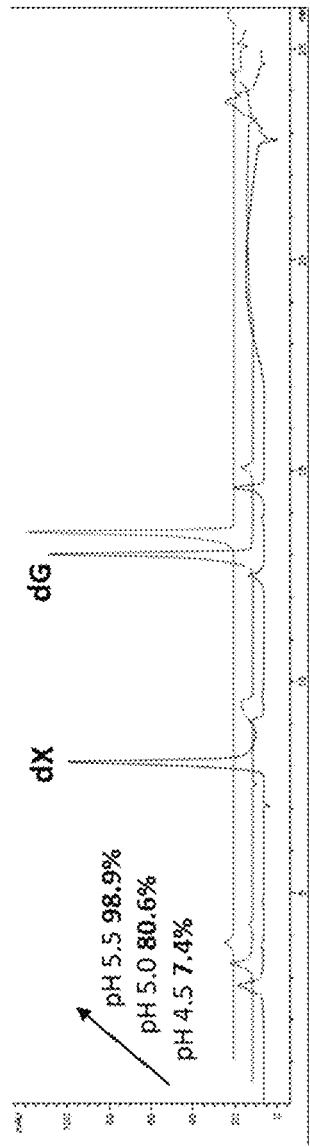
Figure 13:
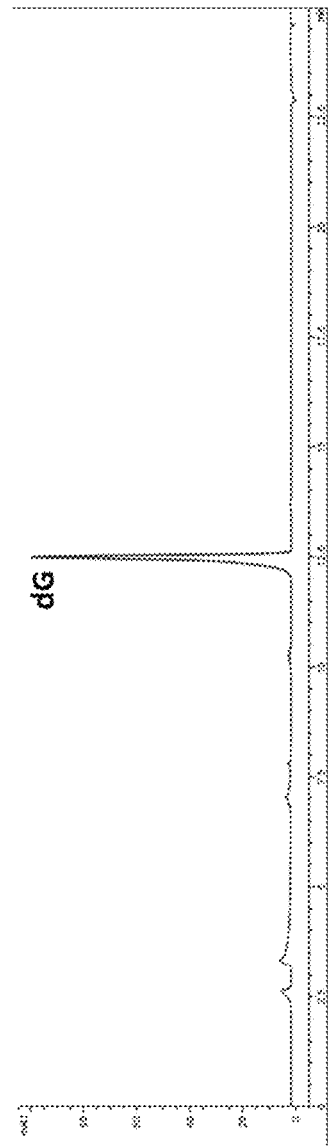
Figure 14:
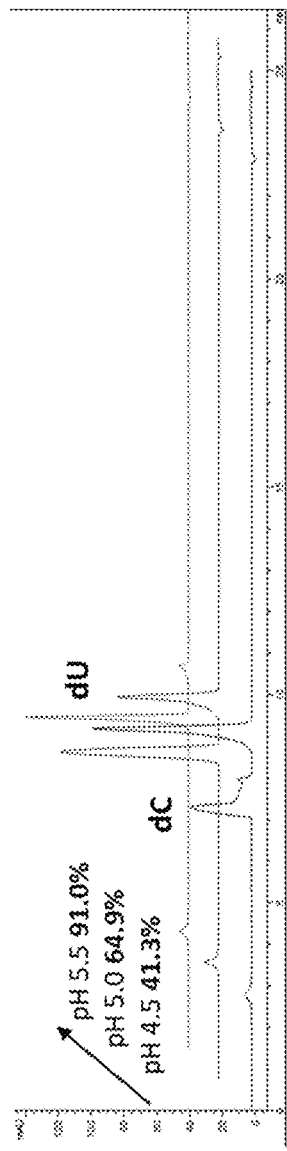
Figure 15:
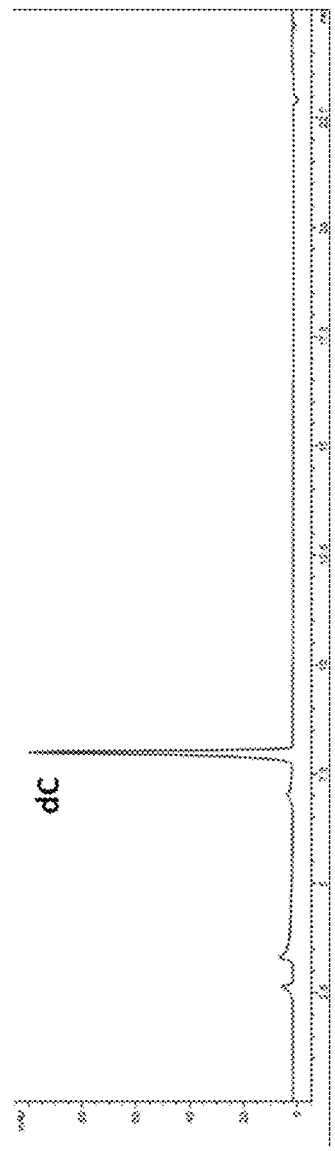

As shown on FIGS. 6 and 7:
Nucleobase impact. All nucleotides demonstrated very similar cleavage rate in every conditions. No pronounced heterocycle effect had been observed.
pH impact. Highest cleavage rate reached in slightly acidic media—pH 5.0 is optimal.
Mg (II) impact. Magnesium salt binds to carbonyl bisphosphonate and precipitates. Magnesium markedly facilitates the cleavage yield at higher pH.
Purity. Unwanted peaks appeared just at higher pH (8.25). For the range pH 5.0-7.0 HPLC profiles look pretty clean with 2 or 1 major peaks. No accumulation of by-products overtime had been observed.

Example 5: Stability Test with Nucleosides 10 mM dA, dT, dG and dC nucleosides were incubated with 0.5M NaNO$_2$ in acetate buffer (pH 4.5, pH 5.0, pH 5.5) and with 0.5 carbonylbisphosphonate at pH 4.5, 5.0, 5.5. After 72 h incubation time, quenching was performed with bicarbonate buffer (pH around 8, i.e. 8.25)/25° C./sealed plate in dark.

An HPLC analysis was then conducted with the following conditions: C18-Gemini 5 μm, 4.6×250 mm (Phenomenex), A: miliQ water, B: 100% ACN. Flow rate 1 mL/min. Gradient elution profile: from 0% to 15% ACN in 5 CV.

The results of these experiments are shown on FIGS. 8 to 15. Corresponding purities for residual nucleosides in the mixtures are given.

As shown on these Figures, for most nucleosides tested, the deprotecting agent of this disclosure (FIGS. 9, 11, 13 and 15) provides much lower degradation of the nucleoside than sodium nitrite (FIGS. 8, 10, 12 and 14).

Example 6: Synthesis of Acetylphosphonic Acid

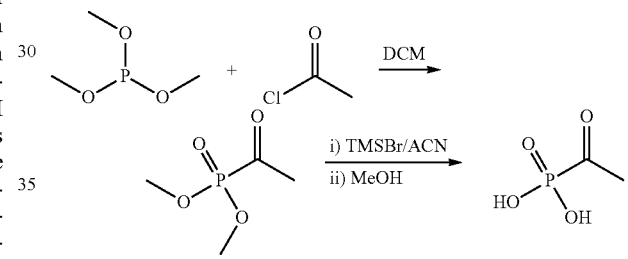

Acetylphosphonic acid was prepared as described in Karaman, R. et al. *Journal of the Chemical Society, Perkin Transactions* 1, 4, 765-774 (1989). This synthesis generally consists of Arbuzov reaction of the corresponding chloroanhydride and trimethyl phosphite, followed by deesterification with trimethylsilyl bromide as described below.

Dimethyl Acetylphosphonate

Acetyl chloride (10 mmol) was dissolved in dry DCM (20 mL) and cooled with an ice bath. Trimethylphosphite (11 mmol) was added dropwise upon stirring to the mixture. After the addition was completed, the cooling bath was removed and stirring was continued for 2 h at ambient temperature. The reaction mixture was concentrated with rotovap to afford colorless liquid, which was further distilled in vacuo (1-2 mmHg) to collect the fraction of the target compound. Yield: 1.37 g (90%) as a colorless liquid.

Acetylphosphonic Acid

Dimethyl heptanoylphosphonate (1.35 g, 9 mmol) was dissolved in dry acetonitrile (25 mL) and trimethylsilyl bromide (2.95 mL, 22.5 mmol) was slowly added to the reaction upon stirring. The reaction was allowed to stir at ambient temperature for 3 h, then evaporated in vacuo and re-evaporated twice with methanol. Yield 1.05 g (95%) as a viscous colorless oil.

Example 7: Deprotection Experiment

Figure 16:
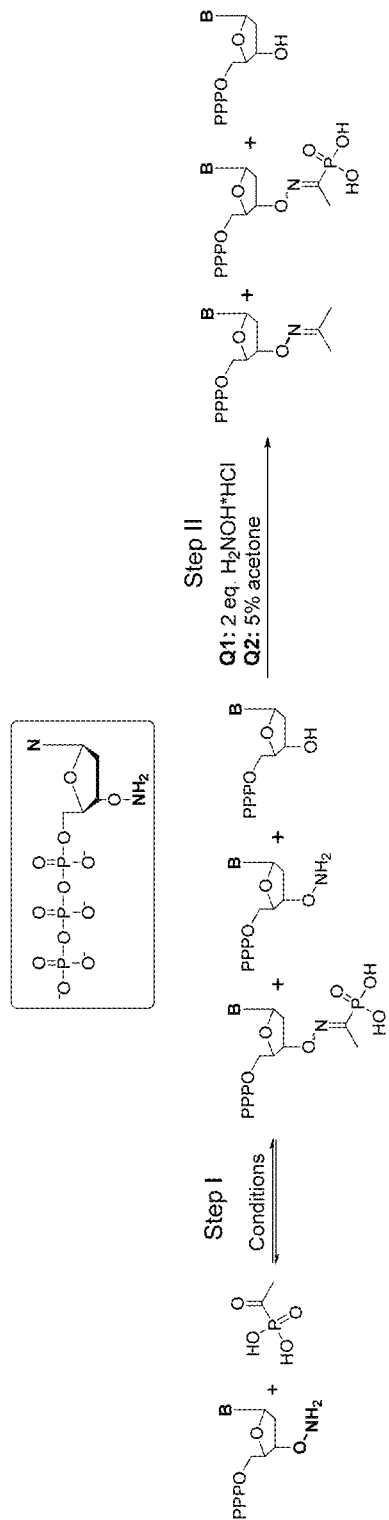
FIG. 16 shows the reaction scheme used in the deprotection study of dTTP-3'-O—$NH_2$ with acetylphosphonic acid used as a deprotecting agent according to this disclosure.

The general scheme of the reaction conducted in this Example is shown on FIG. 16 (Step I: deprotection; Step II: conversion step prior to HPLC).

1 mM solution of dTTP-3'-ONH$_2$ (100 uL) taken in 50 mM sodium acetate (pH 5.0), 50 mM sodium phosphate (pH 6.0), 50 mM sodium phosphate (pH 7.0) or 50 mM sodium bicarbonate (pH around 8, i.e. 8.25) buffers was agitated with ThermoMixer in sealed Eppendorf tubes with 2 eq of acetylphosphonic acid at 25° C. After 5 min/20 min/60 min of incubation the corresponding reaction mixture comprised an adduct (Schiff base) of dTTP-3'-ONH$_2$ and acetylphosphonic acid (dTTP-3'-ONC(CH$_3$)PO$_3$H$_2$) in addition to unreacted dTTP-3'-ONH$_2$ and the cleavage product (dTTP-3'-OH). This reaction mixture was quenched with 2 eq. of hydroxylamine hydrochloride in 100 uL of deionized water followed by excess of aqueous 5% acetone. Thereby, non-reacted residual dTTP-ONH$_2$ was converted to an inert acetoxime form—dTTP-OX. The quenched reaction mixtures were analyzed with reversed-phase HPLC as with the following conditions: C18 Xterra 3.5 μm, 4.6×50 mm column (Waters); Buffer A: 50 mM TEAB (pH 8.5), Buffer B: 100% ACN. Gradient elution method: flow rate: 1.5 mL/min, 0-2 min-0% ACN B, 5.3 min-10% ACN, 8 min-30% ACN, 8-10 min-100% ACN.

Figure 17:
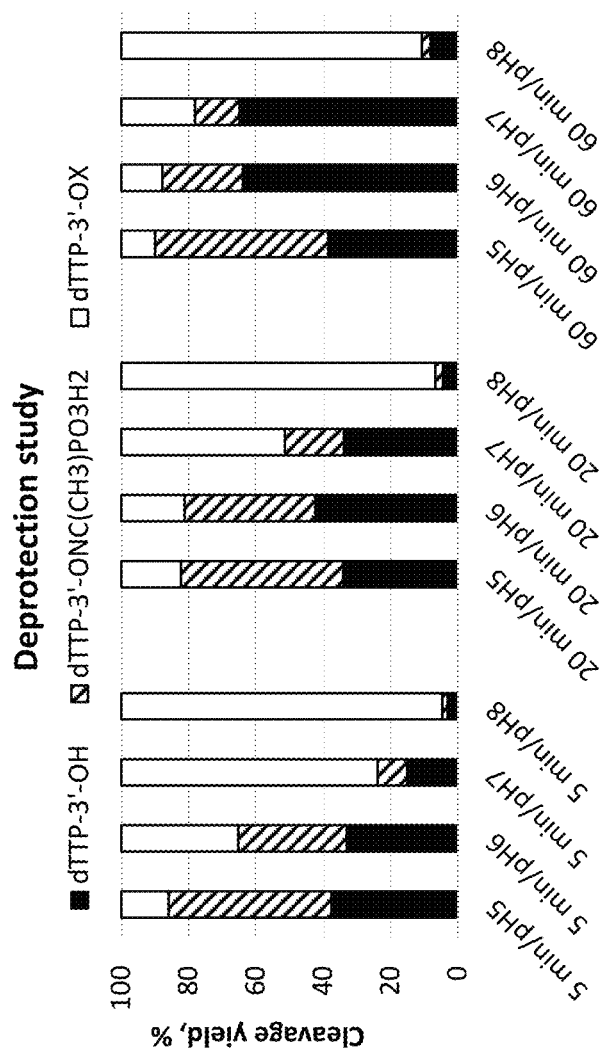
FIG. 17 shows 3'-$ONH_2$ to 3'-OH conversion yield and formation of a stable Schiff base adduct based on the reaction between dTTP-$ONH_2$ and 2 eq of acetylphosphonic acid at different pHs and reaction times.

As shown on FIG. 17, conversion of 3'-ONH$_2$ to 3'-OH reaches about 60% after 60 minutes at pH 6 or 7.

Example 8: Enzymatic DNA Synthesis Experiments

Figure 18:
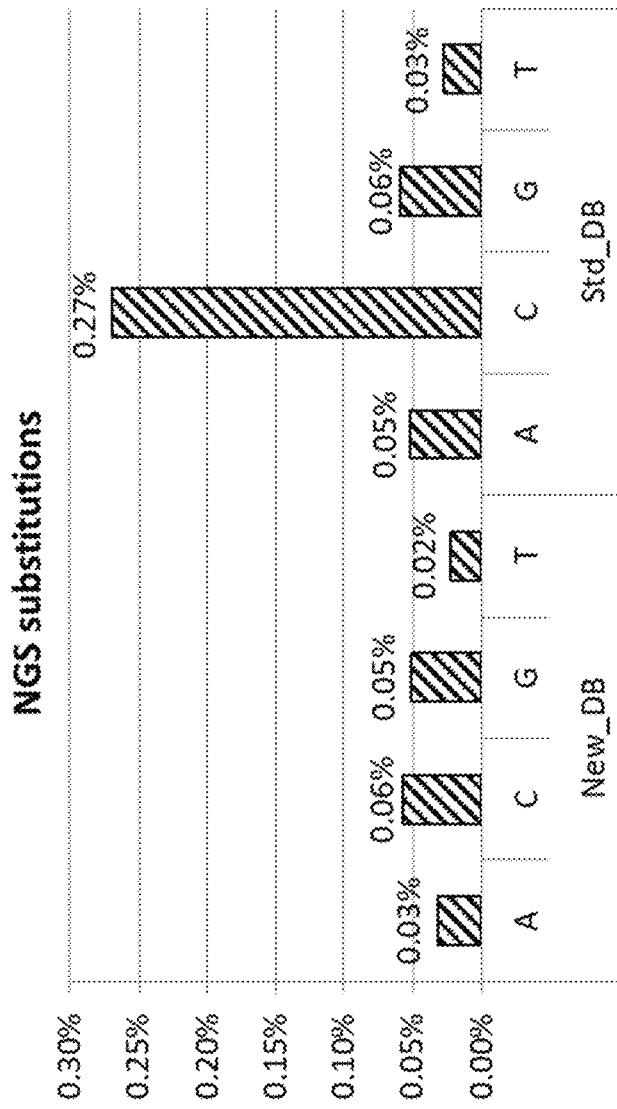
FIG. 18 shows the results of a comparative analysis of 52-mer oligodeoxynucleotide substitution rate synthesized either with carbonylbisphosphonate (New-DB) or aqueous nitrous acid (Std_DB) as deprotecting agents.

Oligodeoxyribonucleotide synthesis was performed in 96-well filter plate according to the standard procedure by using TdT modified enzyme and four deoxynucleotides protected with 3'-ONH$_2$ groups (dTTP-ONH$_2$, dATP-ONH$_2$, dGTP-ONH$_2$, dCTP-ONH$_2$). Both elongation and deprotection steps were performed in the same conditions for both nitrous acid at slightly acidic pH and carbonylbisphosphonate as deprotection buffers. A pool of 24 52-mer oligonucleotides (SEQ ID NO: 1-24) was synthesized in 2 repeats, desalted by precipitation and analyzed by Next Generation Sequencing (NGS). Values of nucleobase substitutions for both types of deprotection buffer (carbonylbisphosphonic acid and nitrous acid) are shown on FIG. 18.

As shown on this Figure, nitrous acid leads to more alterations in the structure of nucleobases, especially transamination of cytosine (C), than the deprotecting agent of this disclosure, and thus to a higher error rate in NGS.

Example 9: Synthesis of Heptanoyl Phosphonic Acid

The synthesis was reproduced from Karaman, R. et al, *Journal of the Chemical Society*, Perkin Transactions 1, 4, 765-774 (1989) with minor changes in the procedure as described below.

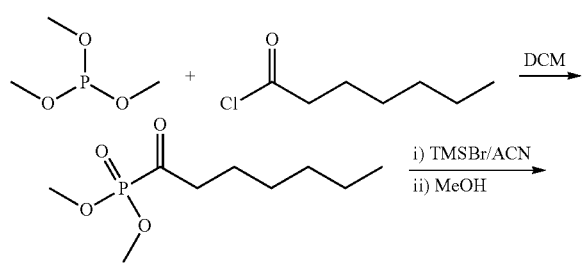

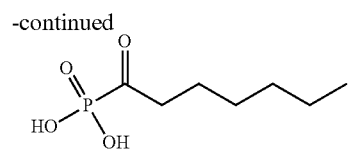

Dimethyl Heptanoylphosphonate

Heptanoyl chloride (10 mmol) was dissolved in dry DCM (20 mL) and cooled with an ice bath. Trimethylphosphite (11 mmol) was added dropwise upon stirring to the mixture. After the addition was completed, the cooling bath was removed and stirring was continued for 2 h at ambient temperature. The reaction mixture was concentrated with rotovap to afford colorless oil, which was further distilled in vacuo (0.2 mmHg) to collect the fraction of the target compound. Yield: 1.84 g (82%) as a viscous colorless liquid.

Heptanoylphosphonic Acid

Dimethyl heptanoylphosphonate (1.8 g, 8.1 mmol) was dissolved in dry acetonitrile (25 mL) and trimethylsilyl bromide (2.67 mL, 20.3 mmol) was slowly added to the reaction upon stirring. The reaction was allowed to stir at ambient temperature for 3 h, then evaporated in vacuo and re-evaporated twice with methanol. The residual oil was taken in water (50 mL) and ethyl acetate (50 mL) in a separating funnel. The organic layer was separated and concentrated in vacuo. Yield 1.08 g (69%) as a white solid.

Example 10: Deprotection Experiment

Figure 19:
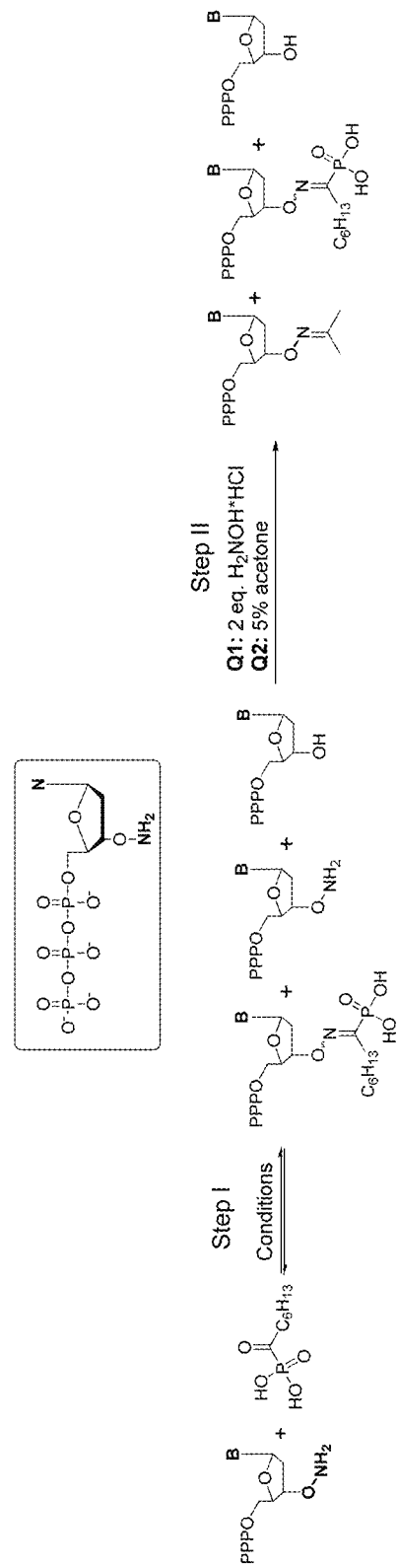
FIG. 19 shows the reaction scheme used in the deprotection study of dTTP-3'-O—$NH_2$ with heptanoylphosphonic acid used as a deprotecting agent according to this disclosure.

The general scheme of the reaction conducted in this Example is shown on FIG. 19 (Step I: deprotection; Step II: conversion step prior to HPLC).

Materials and Methods

The screening tests were performed in a 96-well plate with a reaction volume of 100 uL. Nucleoside triphosphate (dTTP-3'-ONH$_2$) was taken at 1 mM final concentration in one of four 50 mM buffers (A: sodium acetate pH 5.0, B: sodium phosphate pH 6.0, C: sodium phosphate 7.0, D: sodium bicarbonate pH around 8, i.e. 8.25). Heptanoyl phosphonic acid was added to the dTTP solution at 2 mM final concentration and incubated during 5, 20 or 60 mins prior to quenching with 2× concentration of hydroxylamine hydrochloride. The 96-well plate were agitated with Thermomixer at 25° C. or 40° C. Prior to HPLC analysis reaction mixtures were additionally quenched with acetone to convert 3'-ONH$_2$ to acetoxime form. The samples were analyzed by RP-HPLC with gradual gradient of acetonitrile in 50 mM TEAB buffer (pH 8.5). The cleavage rate was determined based on the ratio between dTTP-3'-OH and dTTP-3'-acetoxime.

HPLC Conditions

Xterra RP C18 Column: 4.6*50 mm, (3.5 um silica), Buffer A: 50 mM TEAA (pH 7.0), Buffer B: 100% ACN. Method: 0-2 min-0% ACN B, 6 min-10% ACN, 8 min-30% ACN, 8-10 min-100% ACN. Flowrate: 1.5 mL/min, no loop insert.

Results

Figure 20:
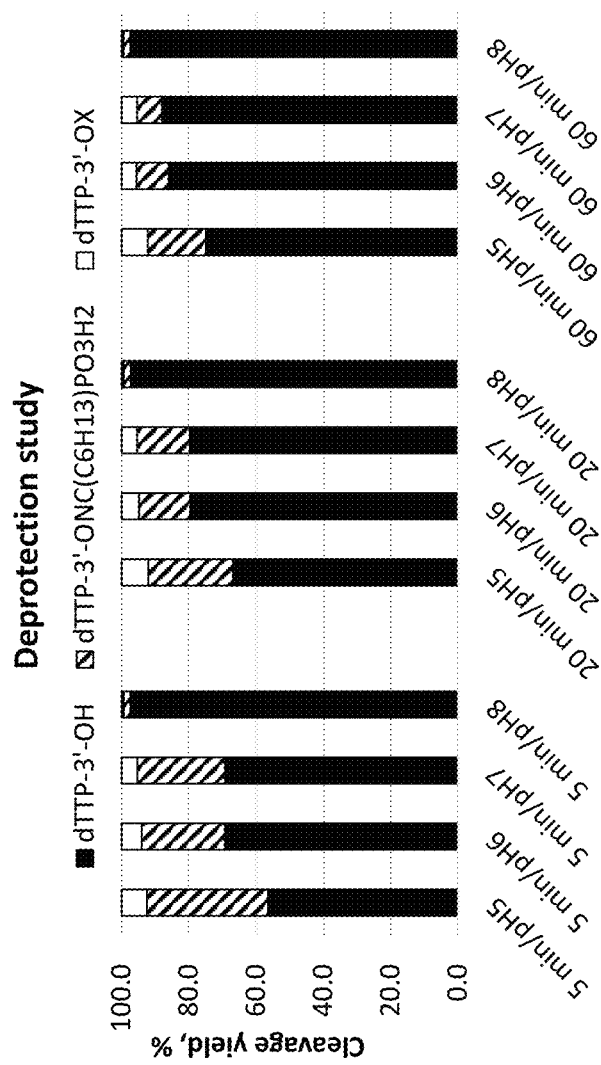
FIG. 20 shows 3'-$ONH_2$ to 3'-OH conversion yield and formation of a stable Schiff base adduct based on the reaction between dTTP-$ONH_2$ and 2 eq of heptanoylphosphonic acid at different pHs and reaction times.

As shown on FIGS. 19 and 20:
pH impact. Highest cleavage rate was reached as pH increased from 5 to about 8-pH 8.25 is optimal.
Purity. Unwanted peaks appeared at lower pH (5-6). For the range of pH 7.0-8.25, the HPLC profile shows 2 or 1 major peaks only.

All references cited within this disclosure are hereby incorporated by reference in their entirety. Certain embodiments have been described herein but are provided as examples only and are not intended to limit the scope of the claims in any way. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method of synthesizing a polynucleotide, the method comprising the steps of:
   (a) providing initiators which are polynucleotides having each a free 3'-hydroxyl;
   (b) repeating in a reaction mixture, until the polynucleotide is formed, cycles of:
      (i) contacting under elongation conditions the initiators or elongated fragments having free 3'-hydroxyls with a 3'-O—NH₂ nucleoside triphosphate and a polymerase, so that the initiators or elongated fragments are elongated by incorporation of a 3'-O-amino nucleoside triphosphate to form 3'-O-amino elongated fragments, and
      (ii) deprotecting the elongated fragments to form elongated fragments having free 3'-hydroxyls;
   wherein the deprotecting is performed by contacting the elongated fragments with an effective amount of at least one phosphonate compound, wherein at least one phosphonate compound is:

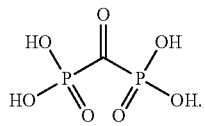

2. The method of claim 1, wherein said effective amount is provided by a concentration of said phosphonate compound in the range of from about 0.1 to about 500 mM, optionally about 0.1 to about 100 mM or about 0.1 to about 200 mM, in an aqueous solution buffered at a pH of from about 4 to about 8, optionally from about 5 to about 7.

3. The method of claim 2, wherein the aqueous solution comprises at least one inorganic salt of a divalent metal.

4. The method of claim 3 wherein the divalent metal is selected from the group consisting of magnesium, calcium, zinc, and copper, optionally wherein the at least one inorganic salt is magnesium sulfate.

5. The method of claim 1, wherein the polymerase is a template-independent polymerase.

6. The method of claim 5, wherein the template-independent polymerase is Terminal Deoxynucleotidyl Transferase (TdT).

7. The method of claim 5, wherein the method is an enzymatic DNA synthesis.

8. The method of claim 5, wherein the method is an enzymatic RNA synthesis.

9. The method of claim 1, wherein the polymerase is a template-dependent polymerase.

10. The method of claim 9, wherein the method is sequencing DNA.

11. The method of claim 10, wherein the method is sequencing-by-synthesis (SBS) or sequencing-by-binding (SBB).

12. The method of claim 11, wherein the method is sequencing-by-synthesis comprising the steps of:
   (a) providing initiators which are polynucleotides having each a free 3'-hydroxyl;
   (b) repeating in a reaction mixture, until the polynucleotide is formed, cycles of:
      (i) contacting under elongation conditions the initiators or elongated fragments having free 3'-hydroxyls with a fluorescently labelled 3'-O—$NH_2$ nucleotide and a polymerase, so that the initiators or elongated fragments are elongated by incorporation of a fluorescently labelled 3'-O-amino nucleotide to form 3'-O-amino elongated fragments,
      (ii) washing away excess of non-incorporated nucleotides,
      (iii) reading the fluorescence signal to know the nucleotide incorporated,
      (iv) removing the fluorescent label and using the at least one phosphonate compound to remove the 3'-O-amino group to form elongated fragments having free 3'-hydroxyls, and
      (v) repeating steps (i) to (iv) until the end of sequencing.

13. The method of claim 11, wherein the method is sequencing-by-binding comprising the steps of:
   (a) providing initiators which are polynucleotides having each a free 3'-hydroxyl; and,
   (b) repeating in a reaction mixture, until the polynucleotide is formed, cycles of:
      (i) contacting under elongation conditions the initiators or elongated fragments having free 3'-hydroxyls with a 3'-O—$NH_2$ nucleotide and a polymerase, so that the initiators or elongated fragments are elongated by incorporation of 3'-O-amino nucleotide to form 3'-O-amino elongated fragments,
      (ii) contacting under elongation conditions the 3'-O-amino elongated fragments with a fluorescently labelled nucleotide and a polymerase, so that the fluorescently labelled nucleotide is bound in the active site of the polymerase,
      (iii) washing away unbound fluorescently labelled nucleotides,
      (iv) reading the fluorescence signal to know the nucleotides bound in the active site,
      (v) washing away the bound nucleotides,
      (vi) deprotecting the 3'-O—$NH_2$ polynucleotide with the at least one phosphonate compound, and
      (vii) repeating steps (i) to (vi) until the end of sequencing.

* * * * *

```
                              SEQUENCE LISTING

Sequence total quantity: 24
SEQ ID NO: 1            moltype = DNA   length = 52
FEATURE                 Location/Qualifiers
source                  1..52
                        mol_type = other DNA
                        organism = synthetic construct
SEQUENCE: 1
acgacctaca gaacaaaccg gggttccgag cggtaatagc aacaccaacg gg            52

SEQ ID NO: 2            moltype = DNA   length = 52
FEATURE                 Location/Qualifiers
source                  1..52
                        mol_type = other DNA
                        organism = synthetic construct
SEQUENCE: 2
actaatcctt ggggagagat ctatatacta atacggtgaa ctctggggcc gg            52

SEQ ID NO: 3            moltype = DNA   length = 52
FEATURE                 Location/Qualifiers
source                  1..52
                        mol_type = other DNA
                        organism = synthetic construct
SEQUENCE: 3
gtctctgcgg aggaagacac ttcggcttcg cggaatcgac tatcaggcgg gg            52

SEQ ID NO: 4            moltype = DNA   length = 52
FEATURE                 Location/Qualifiers
source                  1..52
                        mol_type = other DNA
                        organism = synthetic construct
SEQUENCE: 4
gacttatccc ccaaggattt gtacgtgact ccttataagg tatgtcgtgc gg            52

SEQ ID NO: 5            moltype = DNA   length = 52
FEATURE                 Location/Qualifiers
source                  1..52
                        mol_type = other DNA
                        organism = synthetic construct
SEQUENCE: 5
ttcgtctatt cctggtggac agttataagt tctcgaccca ttgacgcctt gg            52

SEQ ID NO: 6            moltype = DNA   length = 52
FEATURE                 Location/Qualifiers
source                  1..52
                        mol_type = other DNA
                        organism = synthetic construct
SEQUENCE: 6
tagtagcaag agcacctcct tctagtcttt acccgactga taaccgcgac gg            52

SEQ ID NO: 7            moltype = DNA   length = 52
FEATURE                 Location/Qualifiers
source                  1..52
                        mol_type = other DNA
                        organism = synthetic construct
SEQUENCE: 7
atcaatccta gtacatccgc gataggattt ctagttacta tatcatcagc gg            52

SEQ ID NO: 8            moltype = DNA   length = 52
FEATURE                 Location/Qualifiers
source                  1..52
                        mol_type = other DNA
                        organism = synthetic construct
SEQUENCE: 8
cttgggacta cccaacagcg ttgagtgatc atacacaggt attccagcga gg            52
```

| SEQ ID NO: 9 | moltype = DNA length = 52 |
|---|---|
| FEATURE | Location/Qualifiers |
| source | 1..52 |
| | mol_type = other DNA |
| | organism = synthetic construct |

SEQUENCE: 9
acactgacag tgctcaataa tcacacgaag tctctgtgcg atgattgacc gg    52

| SEQ ID NO: 10 | moltype = DNA length = 52 |
|---|---|
| FEATURE | Location/Qualifiers |
| source | 1..52 |
| | mol_type = other DNA |
| | organism = synthetic construct |

SEQUENCE: 10
gtatggcgcg atgactcgcg cacgctacgg attcacttgc taaatatcac gg    52

| SEQ ID NO: 11 | moltype = DNA length = 52 |
|---|---|
| FEATURE | Location/Qualifiers |
| source | 1..52 |
| | mol_type = other DNA |
| | organism = synthetic construct |

SEQUENCE: 11
agttagtcaa aaccatgtcc tacctaagta aacctcccaa ggaagaaaca gg    52

| SEQ ID NO: 12 | moltype = DNA length = 52 |
|---|---|
| FEATURE | Location/Qualifiers |
| source | 1..52 |
| | mol_type = other DNA |
| | organism = synthetic construct |

SEQUENCE: 12
actggagaga agctatgtat atatatcggc cgcgtcatgc tgcgttgcac gg    52

| SEQ ID NO: 13 | moltype = DNA length = 52 |
|---|---|
| FEATURE | Location/Qualifiers |
| source | 1..52 |
| | mol_type = other DNA |
| | organism = synthetic construct |

SEQUENCE: 13
tctgtgtcgc gccctcgtaa ctgcgttgtt tattttgtcg agataacgtt gg    52

| SEQ ID NO: 14 | moltype = DNA length = 52 |
|---|---|
| FEATURE | Location/Qualifiers |
| source | 1..52 |
| | mol_type = other DNA |
| | organism = synthetic construct |

SEQUENCE: 14
aggggaataa cccatttttt cttgcaacca gaatgtggtt gcctatactg gg    52

| SEQ ID NO: 15 | moltype = DNA length = 52 |
|---|---|
| FEATURE | Location/Qualifiers |
| source | 1..52 |
| | mol_type = other DNA |
| | organism = synthetic construct |

SEQUENCE: 15
gtccaccggt tcttcgccca aacccggacc tcgagggcct gtgcagatag gg    52

| SEQ ID NO: 16 | moltype = DNA length = 52 |
|---|---|
| FEATURE | Location/Qualifiers |
| source | 1..52 |
| | mol_type = other DNA |
| | organism = synthetic construct |

SEQUENCE: 16
aagcagatca aatgtgtaga cggccagcca cctcggaact tatggcagac gg    52

| SEQ ID NO: 17 | moltype = DNA length = 52 |
|---|---|
| FEATURE | Location/Qualifiers |
| source | 1..52 |
| | mol_type = other DNA |
| | organism = synthetic construct |

SEQUENCE: 17
tgatggcggt tcaggcacac aggggtccgt gcggttccgc acagggcaat gg    52

| SEQ ID NO: 18 | moltype = DNA length = 52 |
|---|---|
| FEATURE | Location/Qualifiers |
| source | 1..52 |
| | mol_type = other DNA |
| | organism = synthetic construct |

```
SEQUENCE: 18
tggcgctgtt tcgcgtgaca ttctaaatac ggatgtggca tccgactggg gg          52

SEQ ID NO: 19           moltype = DNA  length = 52
FEATURE                 Location/Qualifiers
source                  1..52
                        mol_type = other DNA
                        organism = synthetic construct
SEQUENCE: 19
catagtacgg ggcgcataag aaacctacgg ccatataaac gcttacgtac gg          52

SEQ ID NO: 20           moltype = DNA  length = 52
FEATURE                 Location/Qualifiers
source                  1..52
                        mol_type = other DNA
                        organism = synthetic construct
SEQUENCE: 20
aataagaaaa ttgaaaccca tattaccgca ataagaatca gtaaagtatg gg          52

SEQ ID NO: 21           moltype = DNA  length = 52
FEATURE                 Location/Qualifiers
source                  1..52
                        mol_type = other DNA
                        organism = synthetic construct
SEQUENCE: 21
aggcctgtcc tatggctagg actctggtca ctgcaaaggg aaaaggcaac gg          52

SEQ ID NO: 22           moltype = DNA  length = 52
FEATURE                 Location/Qualifiers
source                  1..52
                        mol_type = other DNA
                        organism = synthetic construct
SEQUENCE: 22
gcatgaacct ttcgacatct aacctttacc ccaattccgt ctaggcctca gg          52

SEQ ID NO: 23           moltype = DNA  length = 52
FEATURE                 Location/Qualifiers
source                  1..52
                        mol_type = other DNA
                        organism = synthetic construct
SEQUENCE: 23
ggattacggt gtcagctatt taacaacttg acccgtaacg caagttaata gg          52

SEQ ID NO: 24           moltype = DNA  length = 52
FEATURE                 Location/Qualifiers
source                  1..52
                        mol_type = other DNA
                        organism = synthetic construct
SEQUENCE: 24
gattgcgggc gatgggtgag gctaagccag cgataccttg tcaatgactt gg          52
```